United States Patent
Ostoja Starzewski et al.

(10) Patent No.: US 7,169,865 B2
(45) Date of Patent: Jan. 30, 2007

(54) TRANSITION METAL COMPOUNDS HAVING A DONOR-ACCEPTOR INTERACTION AND A SPECIFIC SUBSTITUTION PATTERN

(75) Inventors: Karl-Heinz Aleksander Ostoja Starzewski, Rösrath (DE); Norbert Steinhauser, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/667,711

(22) Filed: Sep. 22, 2003

(65) Prior Publication Data

US 2004/0059073 A1   Mar. 25, 2004

(30) Foreign Application Priority Data

Sep. 23, 2002 (DE) ................. 102 44 214

(51) Int. Cl.
*C08F 4/6392* (2006.01)
*C08F 4/64* (2006.01)
*C08F 10/00* (2006.01)

(52) U.S. Cl. .............. 526/160; 526/131; 526/161; 526/165; 526/348; 526/943; 502/155

(58) Field of Classification Search ............ 526/160, 526/165, 348, 963, 161, 131, 943; 502/155
See application file for complete search history.

(56) References Cited

U.S. PATENT DOCUMENTS

| 5,324,800 | A | 6/1994 | Welborn, Jr. et al. |
|---|---|---|---|
| 5,580,939 | A | 12/1996 | Ewen et al. |
| 5,633,394 | A | 5/1997 | Welborn, Jr. et al. |
| 5,756,417 | A | 5/1998 | De Boer et al. ............ 502/117 |
| 6,156,857 | A | 12/2000 | Starzewski et al. |
| 6,172,169 | B1 | 1/2001 | Starzewski et al. |
| 6,174,974 | B1 | 1/2001 | Starzewski et al. |
| 6,184,320 | B1 | 2/2001 | Starzewski et al. |
| 6,191,241 | B1 | 2/2001 | Starzewski et al. |
| 6,232,413 | B1 | 5/2001 | Starzewski et al. |
| 6,353,064 | B1 * | 3/2002 | Ostoja-Starzewski ....... 526/160 |
| 6,423,659 | B1 | 7/2002 | Starzewski et al. |
| 6,433,112 | B1 | 8/2002 | Ostoja-Starzewski et al. |
| 6,657,027 | B2 | 12/2003 | Ostoja-Starzewski et al. ... 526/161 |
| 2003/0036474 | A1 | 2/2003 | Ostoja-Starzewski et al. ... 502/152 |

FOREIGN PATENT DOCUMENTS

| CA | 2315651 | 7/1999 |
|---|---|---|
| CA | 2159409 | 1/2001 |
| WO | 94/20506 | 9/1994 |

* cited by examiner

Primary Examiner—Caixia Lu
(74) Attorney, Agent, or Firm—Jennifer R. Seng

(57) ABSTRACT

The present invention relates to compounds in which a transition metal is complexed by at least two ligand systems and at least two of the systems are reversibly joined to one another by at least one bridge comprising a donor and an acceptor, wherein at least one fluorenyl ligand is present and at least one substituent on the acceptor group is an alkyl or aryl radical. The invention further relates to the use of these compounds having a donor-acceptor interaction as polymerization catalysts for preparing high molecular weight elastomers.

17 Claims, 1 Drawing Sheet

Figure 1:
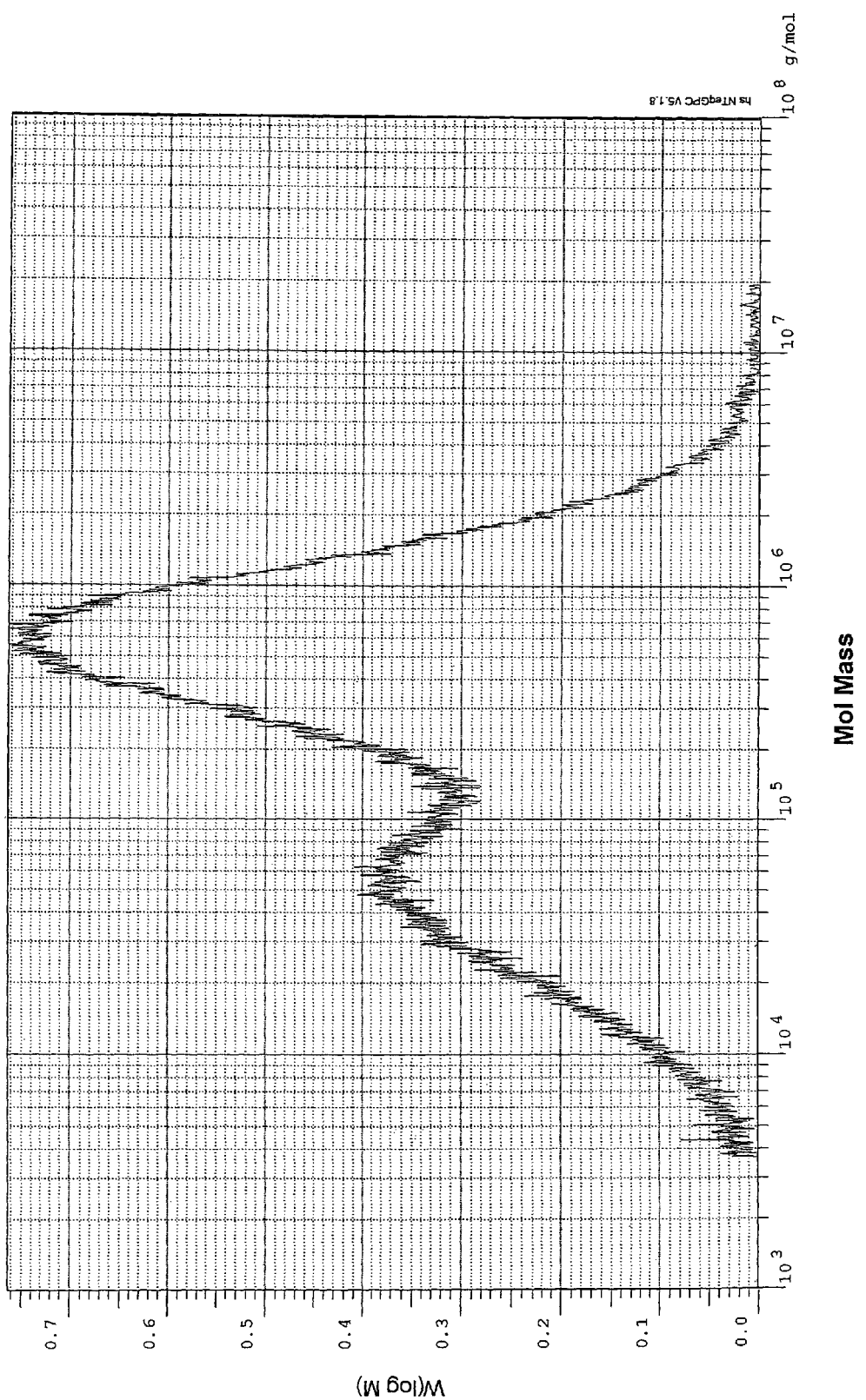

TRANSITION METAL COMPOUNDS HAVING A DONOR-ACCEPTOR INTERACTION AND A SPECIFIC SUBSTITUTION PATTERN

FIELD OF THE INVENTION

The present invention relates to compounds in which a transition metal is complexed by at least two ligand systems and at least two of the systems are reversibly joined to one another by at least one bridge containing a donor and an acceptor, wherein at least one fluorenyl ligand is present and at least one substituent on the acceptor group is an alkyl or aryl radical and transition metal compounds having fluorinated aryl groups on the acceptor atom are excluded. The present invention further relates to the use of these compounds having a donor-acceptor interaction as polymerization catalysts for preparing high molecular weight elastomers.

BACKGROUND OF THE INVENTION

The coordinate bond formed between the donor atom and the acceptor atom generates a positive (partial) charge in the donor group and a negative (partial) charge in the acceptor group:

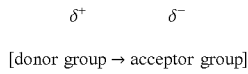

[donor group → acceptor group]

Metallocenes as π complexes and their use as catalysts in the polymerization of olefins have been known for a long time from EP-A-129 368 and the references cited therein. It is also known from EP-A-129 368 that metallocenes in combination with aluminum alkyl/water as cocatalysts are effective systems for the polymerization of ethylene (for example, about 1 mol of trimethylaluminum and 1 mol of water forms methylaluminoxane=MAO). Other stoichiometric ratios have also been employed successfully (WO 94/20506). Metallocenes whose cyclopentadienyl skeletons are covalently bound to one another by means of a bridge are also known.

As an example of the numerous patents and patent applications in this field, mention may be made of EP-A 704 461 in which the bridging group mentioned is a (substituted) methylene group or ethylene group, a silylene group, a substituted silylene group, a substituted germylene group or a substituted phosphine group. In EP-A 704 461, too, bridged metallocenes are envisaged as polymerization catalysts for olefins.

Catalysts having a donor-acceptor interaction and their use as polymerization catalysts are known in principle.

WO-A-98/01455 describes compounds in which a transition metal is complexed by two π systems, in particular aromatic π systems (metallocenes), and the two systems are reversibly joined to one another by means of at least one bridge containing a donor and an acceptor, with the donor and acceptor atoms being bound as substituents to the π systems, and also provides for their use as polymerization catalysts.

WO-A-98/45339 describes compounds in which a transition metal is complexed by two π systems, in particular aromatic π systems (metallocenes), and the two systems are reversibly joined to one another by means of at least one bridge containing a donor and an acceptor, with at least one of the donor or acceptor atoms being part of the associated π system, and also provides for their use as polymerization catalysts.

The patent applications WO-A-98/01483, WO-A-98/01484, WO-A-98/01485, WO-A-98/01486, WO-A-98/01487, WO-A-99/32532 and EP-B1 042 336 describe industrial polymerization processes using the described catalysts having a donor-acceptor interaction.

It is known from these documents that the catalysts having a donor-acceptor interaction can advantageously be used as catalysts for olefin polymerization.

It is not known in the art that metallocenes which have a donor-acceptor interaction can make it possible to carry out polymerizations at elevated temperatures (≧40° C.) so as to give polyolefin elastomers having very high molar masses, and at the same time display a high activity in the presence of small amounts of cocatalyst.

SUMMARY OF THE INVENTION

It is therefore an object of the present invention to provide transition metal compounds which can be used for the polymerization of olefins to give elastomers having very high molar masses both in the presence of small amounts of cocatalyst and at high temperatures.

This object is surprisingly achieved by transition metal compounds having at least two π systems and at least one donor-acceptor interaction between the π systems, wherein at least one π system is a fluorenyl ligand and the transition metal compound bears at least one alkyl or aryl group on at least one acceptor atom and transition metal compounds having fluorinated aryl groups are excepted.

The present invention further provides the reaction product of cocatalysts and transition metal compounds.

In addition, the invention provides a process for the homopolymerization or copolymerization of one or more olefins, cycloolefins, isoolefins, alkynes or diolefins as monomers or for ring-opening polyaddition at from −60 to +250° C., wherein the polymerization is carried out in the presence of at least one transition metal compound or a reaction product.

The present invention further provides for the use of the transition metal compounds of the invention or their reaction products as catalyst components for preparing high molecular weight and ultrahigh molecular weight elastomers.

π systems which can be used for the purposes of the invention in addition to the fluorenyl ligand include substituted and unsubstituted ethylene, allyl, pentadienyl, benzyl, butadiene, benzene, the cyclopentadienyl anion and the species obtained by replacement of at least one carbon atom by a heteroatom. Among the species mentioned, the cyclic species are preferred. More preference is given to the cyclopentadienyl anion. The coordination of such ligands (π systems) to the metal can be of the σ type or of the π type.

The present invention also provides a process for preparing an elastomer including the step of admixing one or more monomers in the presence of at least one transition metal compound having at least two ligands and at least one donor-acceptor interaction between the ligands, wherein at least one ligand is a fluorenyl ligand and the transition metal compound has at least one alkyl or aryl group on at least one acceptor atom and optionally one or more cocatalyst, wherein the process is carried out at a temperature from about −60 to about +250° C., wherein the process produces a polymer having a mean molar mass $M_n$ greater than 500 kg/mol.

In addition, the present invention provides a process for preparing a polyolefin including the step of admixing one or more monomers in the presence of at least one transition metal compound having at least two ligands and at least one donor-acceptor interaction between the ligands, wherein at least one ligand is a fluorenyl ligand and the transition metal compound has at least one alkyl or aryl group on at least one acceptor atom and optionally one or more cocatalyst, wherein the process is carried out at a temperature from about −60 to about +250° C., wherein the process produces polymers having a mean molar mass $M_n$ greater than 500 kg/mol, and optionally one or more cocatalyst, wherein the polyolefin has an $M_n \geq 5 \cdot 10^4$ g/mol.

Accordingly, the present invention provides a process for preparing elastomers with long-chain branching, elastomers with bimodal or multimodal molecular weight distributions. Further the present invention provides a process for preparing elastomeric polypropylene and other elastomers selected from the group consisting of ethylene propylene-diene copolymers, ethylene-butene-diene copolymers, ethylene-hexene-diene copolymers, ethylene-octene-diene copolymers or mixtures thereof.

BRIEF DESCRIPTION OF THE SEVERAL
VIEWS OF THE DRAWING

FIG. 1 provides a graphical illustration of the bimodal mean viscosity molar mass distribution in accord with Example 27 of the present invention wherein two structurally different Donor-Acceptor Metallocenes are present as catalysts in an Ethene-propene copolymerization.

DETAILED DESCRIPTION OF THE
INVENTION

Suitable transition metal compounds having at least one donor-acceptor interaction are the transition metal compounds having a donor-acceptor interaction described in the patent applications WO-A-98/01455, WO-A-98/45339, WO-A-98/01483, WO-A-98/01484, WO-A-98/01485, WO-A-98/01486 and WO-A-98/01487, characterized in that these transition metal compounds have a fluorenyl ligand and bear alkyl and/or aryl groups on the acceptor group.

Useful transition metal compounds include metallocene compounds of the formulae

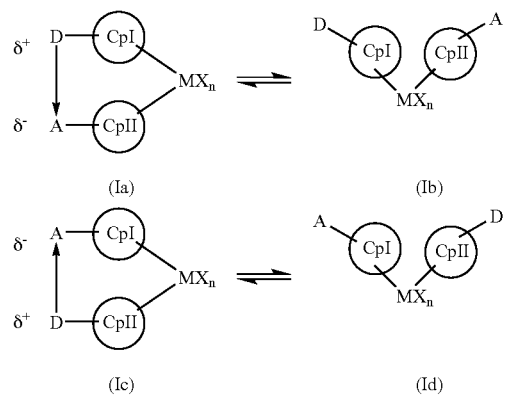

(Ia) (Ib)
(Ic) (Id)

in which one of the Cp ligands
CpI or CpII is a fluorenyl or substituted fluorenyl ligand and the other ligand is the same carbanion or a different carbanion having a cyclopentadienyl-containing structure, where both in the fluorenyl ligand and also in the other ligand from one to all H atoms may be replaced by identical or different radicals selected from the group consisting of linear or branched $C_1$–$C_{20}$-alkyl which may be monohalogenated to perhalogenated, phenyl, vinyl, $C_6$–$C_{12}$-aryl, haloaryl having from 6 to 12 carbon atoms and organometallic substituents such as silyl, trimethylsilyl or ferrocenyl and by 1 or 2 D and A, D is a donor atom which may additionally bear substituents and which in its respective bonding state has at least one free electron pair, A is an acceptor atom which bears at least one alkyl or aryl group, but preferably exclusively alkyl and/or aryl groups, as substituents and which in its respective bonding state has an electron pair gap, where D and A are linked by means of a reversible coordinate bond in such a way that the donor group acquires a positive (partial) charge and the acceptor group acquires a negative (partial) charge, M is a metal of groups 3–7 of the Periodic Table of the Elements in the IUPAC (1985) version, including the lanthanides and actinides, X is an anion equivalent and n is zero, one, two, three or four depending on the charge on M.

One of the CpI and CpII ligands is a fluorenyl or substituted fluorenyl anion. The other ligand preferably has a cyclopentadienyl-containing skeleton, with ligands selected from the group consisting of cyclopentadiene, substituted cyclopentadiene, indene, substituted indene, fluorene and substituted fluorene being preferred. Preference is given to cyclopentadienyl and substituted cyclopentadienyl anions as other ligands.

The number of substituents on CpI and CpII is from 1 to 4 substituents per cyclopentadiene ring or fused-on benzene ring. The substituents can be $C_1$–$C_{20}$-alkyl such as methyl, ethyl, propyl, isopropyl, butyl or isobutyl, hexyl, octyl, decyl, dodecyl, hexadecyl, octadecyl, eicosyl, $C_1$–$C_{20}$-alkoxy such as methoxy, ethoxy, propoxy, isopropoxy, butoxy or isobutoxy, hexoxy, octyloxy, decyloxy, dodecyloxy, hexadecyloxy, octadecyloxy, eicosyloxy, halogen such as fluorine, chlorine or bromine, $C_6$–$C_{12}$-aryl such as phenyl, $C_1$–$C_4$-alkylphenyl such as tolyl, ethylphenyl, (i-)propylphenyl, (i-)butylphenyl, tert-butylphenyl, xylyl, halophenyl such as fluorophenyl, chlorophenyl, bromophenyl, difluorophenyl, trifluorophenyl, tetrafluorophenyl, pentafluorophenyl, pentachlorophenyl, naphthyl or biphenylyl, triorganosilyl such as trimethylsilyl (TMS), triorganostannyl, ferrocenyl and D or A, as defined above. Two of these substituents can in turn be linked so as to form a ring, e.g. as a propane-1,3-diyl unit to form a 5-membered ring or as a butane-1,4-diyl unit to form a 6-membered ring. Furthermore, fusedon aromatic rings can be partially or fully hydrogenated so that only the double bond which forms part of both the fused-on ring and the cyclopentadiene ring remains. Benzene rings as in indene or fluorene may also have one or two further fused-on benzene rings. In addition, the cyclopentadiene or cyclopentadienyl ring and the fused-on benzene ring can share a further benzene ring which is fused onto both systems. Such cyclopentadiene skeletons are in the form of their anions which are excellent ligands for transition metals, with each cyclopentadienyl carbanion in the abovementioned, substituted or unsubstituted form balancing one positive charge of the central metal in the complex.

Specific examples of such carbanions include: cyclopentadienyl, methylcyclopentadienyl, 1,2-dimethylcyclopentadienyl, 1,3-dimethylcyclo-pentadienyl, indenyl, phenylindenyl, 1,2-diethylcyclopentadienyl, tetramethylcyclopentadienyl, ethylcyclopentadienyl, n-butylcyclopentadienyl, n-octylcyclopenta-dienyl, β-phenylpropylcyclopentadienyl, tetrahydroindenyl, propylcyclopentadienyl, t-butylcyclopentadienyl, benzylcyclopentadienyl, diphenylmethylcyclopentadienyl, trimethylgermylcyclopentadienyl, trimethyl-stannylcyclopentadienyl, trifluoromethylcyclopentadienyl, trimethylsilyl-cyclopentadienyl, pentamethylcyclopentadienyl, fluorenyl, tetrahydrofluorenyl or octahydrofluorenyl, fluorenyls and indenyls which are benzo-fused on the six-membered ring, N,N-dimethylaminocyclopentadienyl, dimethylphosphinocyclo-pentadienyl, methoxycyclopentadienyl, trimethylsiloxycyclopentadienyl, dimethylboranylcyclopentadienyl, (N,N-dimethylaminomethyl)cyclopentadienyl.

Depending on the charge on M, the index n takes on the value zero, one, two, three or four, preferably zero, one or two, since the abovementioned metals of groups 3–7 can, depending, inter alia, on the subgroups to which they belong, have valencies/charges of from two to six, preferably from two to four, of which two are in each case balanced by the carbanions of the metallocene compound. Accordingly, the index n is one in the case of $La^{3+}$ and is two in the case of $Zr^{4+}$; in the case of $Sm^{2+}$, n=zero.

WO-A-98/01455 discloses the process for preparation of the compounds of the formula (I).

Further suitable metallocene compounds are compounds of the formula (II)

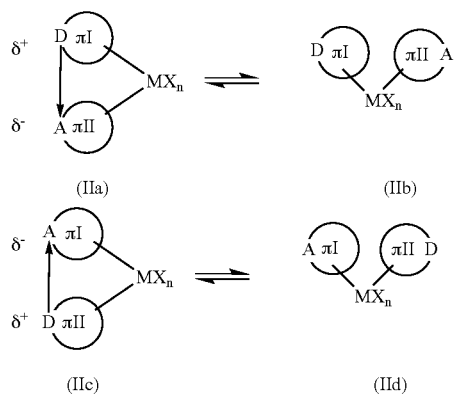

in which one of the π systems

πI and πII is a fluorenyl or substituted fluorenyl ligand and the other is the same π system or a different charged or electrically neutral π system, with both ligands being able to be fused with one or two unsaturated or saturated five- or six-membered rings, D is a donor atom which is a substituent on πI/πII or part of the π system of πI/πII and which in its respective bonding state has at least one free electron pair, A is an acceptor atom which is a substituent of πI/πII or part of the π system of πI/πII and which in its respective bonding state has an electron pair gap, where D and A are linked by means of a reversible coordinate bond in such a way that the donor group bears a positive (partial) charge and the acceptor group bears a negative (partial) charge and at least one of D and A is part of the respective associated π system, where D may in turn bear substituents, and A bears at least one alkyl and/or aryl group, but preferably exclusively alkyl or aryl groups, as substituents, where each π system or each fused-on ring system may contain one or more D or A and where, in πI and πII in the unfused or fused form, one or all H atoms of the π system may, independently of one another, be replaced by identical or different substituents selected from the group consisting of linear or branched $C_1$–$C_{20}$-alkyl which may be monohalogenated to perhalogenated, phenyl, vinyl, $C_6$–$C_{12}$-aryl, haloaryl having from 6 to 12 carbon atoms and by one or two D and A, so that the reversible coordinate D→A bond is formed (i) between D and A which are both parts of the respective π system or the fused-on ring system, or (ii) of which D or A is part of the π system or the fused-on ring system and the other is a substituent on the unfused π system or the fused-on ring system or (iii) both D and A are substituents of this type, where in the case of (iii) at least one additional D or A or both is/are parts of the π system or the fused-on ring system, M is a metal of groups 3–7 of the Periodic Table of the Elements in the IUPAC (1985) version, including the lanthanides and actinides, X is an anion equivalent and n is zero, one, two, three or four, depending on the charges on M and on πI and πII.

According to the present invention, one π system is a substituted or unsubstituted fluorenyl while the other can be a substituted or unsubstituted ethylene, allyl, pentadienyl, benzyl, butadiene, benzene, the cyclopentadienyl anion or the species obtained by replacement of at least one carbon atom by a heteroatom. Among the species mentioned, the cyclic species are preferred. More preference is given to the cyclopentadienyl anion and the substituted cyclopentadienyl anion as π system other than fluorenyl. The coordination of such ligands (π systems) to the metal can be of the σ type or of the π type.

Preference is also given to sandwich structures in which the other ligand is selected from the group consisting of the π system group cyclopentadienyl (cp), indenyl (ind) and fluorenyl (flu).

cp-flu
ind-flu
flu-flu

More preference is given to the combination cp-flu. In a preferred embodiment, one carbon atom of the fluorenyl ligand is replaced by a donor heteroatom so that D is part of a π system (flu) and A is a substituent of the other π system. Examples of such heterofluorenyl ligands are the azafluorenyl anion (carbazolyl)

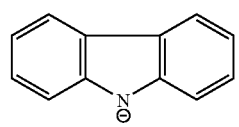

or the phosphafluorenyl anion (dibenzophospholyl)

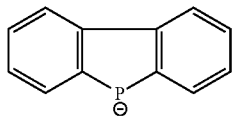

Depending on the charge on M, the index n takes on the value zero, one, two, three or four, preferably zero, one or two, since the abovementioned transition metals of groups 3–7 can, depending, inter alia, on the subgroups to which they belong, have valencies/charges of from two to six, preferably from two to four, of which two are in each case balanced by the carbanions of the metallocene compound. Accordingly, the index n is one in the case of $La^{3+}$ and is two in the case of $Zr^{4+}$; in the case of $Sm^{2+}$, n=zero. More preference is given to compounds of the formula (I).

In the formation of the metallocene structure as in the above formula (I) or (II), one positive charge of the transition metal M is balanced by one cyclopentadienyl-containing carbanion. Remaining positive charges on the central atom M are balanced by further, usually monovalent, anions X of which two identical or different anions may also be linked to one another (dianions

for example monovalent or divalent negative radicals derived from identical or different, linear or branched, saturated or unsaturated hydrocarbons, amines, phosphines, thioalcohols, alcohols or phenols. Simple anions such as $CR_3^-$, $NR_2^-$, $PR_2^-$, $OR^-$, $SR^-$, etc., can be linked by saturated or unsaturated hydrocarbon or silane bridges to form dianions in which the number of bridging atoms can be 0, 1, 2, 3, 4, 5 or 6. Preference is given to from 0 to 4 bridging atoms, more preferably 1 or 2 bridging atoms. The bridging atoms may bear not only H atoms but also further hydrocarbon substituents R. Examples of bridges between simple anions are —$CH_2$—, —$CH_2$—$CH_2$—, —$(CH_2)_3$—, —CH=CH—, —$(CH=CH)_2$—, —CH=CH—$CH_2$—, —$CH_2$—CH=CH—$CH_2$—Si$(CH_3)_2$—, —C$(CH_3)_2$—. Examples of X are: hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, methylethylamino, di-t-butylamino, diphenylamino, diphenylphosphino, dicyclohexylphosphino, dimethylphosphino, methylidene, ethylidene, propylidene and the ethylene glycol dianion. Examples of dianions are 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl1,3-butadienediyl, 1,4-bis(trimethylsilyl)-1,3-butadienediyl, 1,3-butadienediyl. Particular preference is given to 1,4-diphenyl-1,3-butadienediyl, 1,3-pentadienediyl, 1,4-dibenzyl-1,3-butadienediyl, 2,4-hexadienediyl, 3-methyl-1,3-pentadienediyl, 1,4-ditolyl-1,3-butadienediyl and 1,4-bis(trimethylsilyl)-1,3-butadienediyl. Further examples of dianions are ones containing heteroatoms, for instance of the structure

where the bridge has the meaning given above. In addition, weakly coordinating or noncoordinating anions or singly negatively charged anions of the type CpI, CpII, πI, πII with the above-described possible substituents which may bear additional D or A substituents are preferred for balancing the charge.

The compounds of the formula (II) can be prepared as described in WO-A-98/45339.

Apart from the obligatory first donor-acceptor bond between D and A in the formulae (I) and (II), further donor-acceptor bonds may be formed when additional atoms D and/or A are present as substituents in the respective cyclopentadiene systems. All donor-acceptor bonds are characterized by their above-described reversibility. In the case of a plurality of atoms D and/or A, these can occupy various positions among those mentioned. Accordingly, the present invention encompasses both the bridged molecular states and the unbridged states. The number of groups D can be equal to or different from the number of groups A. Preference is given to the ligands, more preferably CpI and CpII, being linked via only one donor-acceptor bridge.

Apart from the D/A bridges according to the present invention, covalent bridges can also be present in the formulae (I) and (II). In this case, the D/A bridges increase the stereorigidity and the thermal stability of the catalyst. Changing between closed and open D/A bonds makes it possible to obtain sequence polymers having a higher and lower stereoregularity. In the case of copolymers, such sequences can have different chemical compositions.

Suitable donor groups in the formulae (I) and (II) are, preferably, ones in which the donor atom D is an element of group 15, 16 or 17 of the Periodic Table of the Elements and has at least one free electron pair and in the case of the donor atom being an element of group 15 it may be bound to substituents and in the case of the donor atom being an element of group 16 it may be bound to a substituent; donor atoms of group 17 do not bear any substituents. This is made clear by the examples of phosphorus P, oxygen O and chlorine Cl as donor atoms, where "Subst." represents such a substituent and "-Cp" represents the bond to the cyclopentadienyl-containing carbanion, a stroke with an arrow represents a coordinate bond in the formula (I) or (II) and other strokes represent electron pairs:

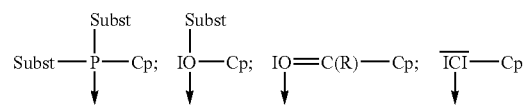

Suitable acceptor groups in the formulae (I) and (II) are, preferably, ones whose acceptor atom A is an element of group 13 of the Periodic Table of the Elements (IUPAC 1985 version), e.g. boron, aluminum, gallium, indium or thallium, and is bound to substituents and has an electron gap. D and A are linked via a coordinate bond, also referred to as a dative bond, with D acquiring a positive (partial) charge and A acquiring a negative (partial) charge.

A distinction is accordingly made between the donor atom D and the donor group and between the acceptor atom A and the acceptor group. The coordinate bond D→A is established between the donor atom D and the acceptor atom A. The donor group is the unit made up of the donor atom D, any substituents present and the electron pairs present; correspondingly, the acceptor group is the unit made up of the acceptor atom A, the substituents and the electron gaps present.

Donor groups are ones in which the free electron pair is localized on N, P, As, Sb, Bi, O, S, Se, Te, F, Cl, Br, I; among these, preference is given to N, P, O, S. Examples of donor groups include: $(CH_3)_2N-$, $(C_2H_5)_2N-$, $(C_3H_7)_2N-$, $(C_4H_9)_2N-$, $(C_6H_5)_2N-$, $(CH_3)_2P-$, $(C_2H_5)_2P-$, $(C_3H_7)_2 P-$, $(i-C_3H_7)_2P-$, $(C_4H_9)_2P-$, $(t-C_4H_9)P-$, $(cyclohexyl)_2 P-$, $(C_6H_5)_2P-$, $(CH_3)(C_6H_5)P-$, $(CH_3O)_2 P-$, $(C_2H_5O)_2P-$, $(C_6H_5O)_2P-$, $(CH_3-C_6H_4O)_2P-$, $((CH_3)_2 N)_2P-$, methyl-containing phosphino groups, $CH_3O-$, $CH_3S-$, $C_6H_5S-$, $-C(C_6H_5)=O$, $-C(CH_3)=O$, $-OSi(CH_3)_3$, $-OSi(CH_3)_2$-t-buty which N and P each bear a free electron pair and O and S bear two free electron pairs and double-bonded oxygen is bound via a spacer group, and also systems such as the pyrrolidone ring in which ring atoms other than N likewise act as spacers.

Acceptor groups are ones in which an electron pair gap is present on B, Al, Ga, In or Tl, preferably B, Al or Ga; examples include: $(C_6H_5)_2B-$, $(C_6H_5)(alkyl)B-$, $(C_6H_5)HB-$, $(CH_3)(C_6H_5)B-$, $(vinyl)(C_6H_5)B-$, $(benzyl)(C_6H_5)B-$, $Cl(C_6H_5)B-$, $(CH_3O)(C_6H_5)B-$, $Cl(C_6H_5)Al-$, $(alkyl)(C_6H_5)Al-$, $(C_6H_5)(C_6H_5)Al-$, $(C_6H_5)_2Al-$, $(C_6H_5)Ga-$, $(C_6H_5)(alkyl)Ga-$, $(CH_3)_2B-$, $(C_2H_5)_2B-$, $(CH_3)_2Al-$, $(C_2H_5)_2Al-$, $(i-C_3H_7)_2Al-$, $(C_4H_9)_2Al-$.

Examples of substituents on the donor atoms N, P, As, Sb, Bi, O, S, Se and Te and on the acceptor atoms B, Al, Ga, In and Tl are: $C_1$–$C_{12}$-(cyclo)alkyl such as methyl, ethyl, propyl, i-propyl, cyclopropyl, butyl, i-butyl, tert-butyl, cyclobutyl, pentyl, neopentyl, cyclopentyl, hexyl, cyclohexyl, the isomeric heptyls, octyls, nonyls, decyls, undecyls, dodecyls; the corresponding $C_1$–$C_{12}$-alkoxy groups; vinyl, butenyl, allyl; $C_6$–$C_{12}$-aryl such as phenyl, naphthyl or biphenylyl, benzyl, which may be substituted by 1 or 2 $C_1$–$C_4$-alkyl groups, $C_1$–$C_4$-alkoxy groups, sulphonate or nitro groups, $C_1$–$C_6$-alkylcarboxy, $C_1$–$C_6$-alkylcarbonyl or cyano (e.g. tri($C_1$–$C_{20}$-alkyl)silyl, tri($C_6$–$C_{12}$-aryl)silyl and analogous constituents with which those skilled in the art are familiar); analogous aryloxy groups; indenyl; halogen such as Cl, Br and I, 1-thienyl, disubstituted amino such as $(C_1$–$C_{12}$-alkyl$)_2$amino, diphenylamino, tris$(C_1$–$C_{12}$-alkyl) silyl, $NaSO_3$-aryl such as $NaSO_3$-phenyl and $NaSO_3$-tolyl, $C_6H_5-C\equiv C-$; aliphatic and aromatic $C_1$–$C_{20}$-silyl whose alkyl substituents may be, in addition to those mentioned above, octyl, decyl, dodecyl, stearyl or eicosyl and whose aryl substituents may be phenyl, tolyl, xylyl, naphthyl or biphenylyl; and substituted silyl groups which are bound via $-CH_2-$ to the donor atom or the acceptor atom, for example $(CH_3)_3SiCH_2-$, $(C_1$–$C_{12}$-alkyl)(phenyl)amino, $(C_1$–$C_{12}$-alkylnaphthyl)amino, $(C_1$–$C_{12}$-alkylphenyl$)_2$ amino, $C_6$–$C_{12}$-aryloxy based on the abovementioned aryl groups. Preferred substituents include: $C_1$–$C_6$-alkyl, $C_5$–$C_6$-cycloalkyl, phenyl, tolyl, $C_1$–$C_6$-alkoxy, $C_6$–$C_{12}$aryloxy, vinyl, allyl, benzyl, Cl, Br, di($C_1$–$C_6$-alkyl)amino, diphenylamino, but with the acceptor atom bearing at least one alkyl and/or aryl substituent, preferably two alkyl and/or aryl substituents. In the case of the donor atom, the substituents may be further substituted by halogens (e.g. F, perfluorophenyl), m,m'-bis(trifluoromethyl)phenyl.

It is preferred that all substituents on the acceptor group are alkyl and/or aryl groups.

An element of group 13 of the PTE in the IUPAC 1985 version is preferably present in the acceptor group.

For the purposes of the present invention, aryl groups are all monocyclic or polycyclic alkyl radicals known to those skilled in the art, preferably ones having from 6 to 13 carbon atoms, e.g. phenyl, naphthyl, fluorenyl, indenyl, which may in turn be substituted. More preference is given to phenyl groups. Substituents on the aryl groups can be identical or different and are selected independently from the group consisting of hydrogen, $C_1$–$C_{20}$-alkyl such as methyl, ethyl, propyl, isopropyl, butyl or isobutyl, hexyl, octyl, decyl, dodecyl, hexadecyl, octadecyl, eicosyl, $C_1$–$C_{20}$-alkoxy such as methoxy, ethoxy, propoxy, isopropoxy, butoxy or isobutoxy, hexoxy, octyloxy, decyloxy, dodecyloxy, hexadecyloxy, octadecyloxy, eicosyloxy, halogen, such as chlorine or bromine, $C_6$–$C_{12}$-aryl such as phenyl, $C_1$–$C_4$-alkylphenyl such as tolyly, ethylphenyl, (i-)propylphenyl, (i-tert-)butylphenyl, xylyl, halophenyl such as chlorophenyl, bromophenyl, naphthyl and biphenylyl, triorganosilyl such as trimethylsilyl (TMS), ferrocenyl and D or A, as defined above. Fluorine-substituted aryl groups can only be used as substituents for the donor atom.

Further suitable donor and acceptor groups are groups of this type which contain chiral centres or in which two substituents together with the D or A atom form a ring.

The present invention further provides for the use of the novel transition metal compounds which have a donor-acceptor interaction and have a fluorenyl ligand and bear an alkyl and/or aryl group on at least one acceptor group in a process for the homopolymerization or copolymerization of one or more olefins, i-olefins, alkynes or diolefins as monomers or for ring-opening polyaddition. The process can be carried out in the gas, solution, bulk, high-pressure or slurry phase at from −60 to +250° C., preferably up to +200° C., and from 0.5 to 5000 bar, preferably from 1 to 3000 bar, and in the presence or absence of saturated or aromatic hydrocarbons or saturated or aromatic halogenated hydrocarbons and in the presence or absence of hydrogen. The present invention further provides a process for preparing polymers with or without a bimodal molar mass distribution. For this purpose, a further transition metal compound having a donor-acceptor interaction is introduced into the process using the transition metal compounds of the present invention. It is also possible to use a transition metal compound without donor-acceptor interaction as a further transition metal compound. The two transition metal compounds present in the reaction mixture form two different polymer fractions. The polymer fractions can be controlled by means of the ratio of the transition metal compounds used. The amount of transition metal compounds of the invention which is used is 1 mol per $10^1$–$10^{12}$ mol of all monomers used, and the polymerization can also be carried out in the presence of cocatalysts such as Lewis acids, Brönsted acids or Pearson acids or additionally in the presence of Lewis bases.

Examples of such Lewis acids include boranes or alanes, e.g. aluminum alkyls, aluminum halides, aluminum alkoxides, aluminoxanes, organoboron compounds, boron halides, boric esters, boroxanes or boron or aluminum compounds which contain both halide and alkyl or aryl or alkoxide substituents, and also mixtures thereof or the triphenylmethyl cation. Aluminoxanes or mixtures of aluminumcontaining Lewis acids with water are particularly preferred. On the basis of present-day knowledge, all acids act as ionizing agents which form a metallocenium cation whose charge is balanced by a bulky, weakly coordinating anion. The present invention further provides the reaction products of such ionizing agents with novel compounds of the formula (I) or (II). They can be described by the formulae (III) or (IV)

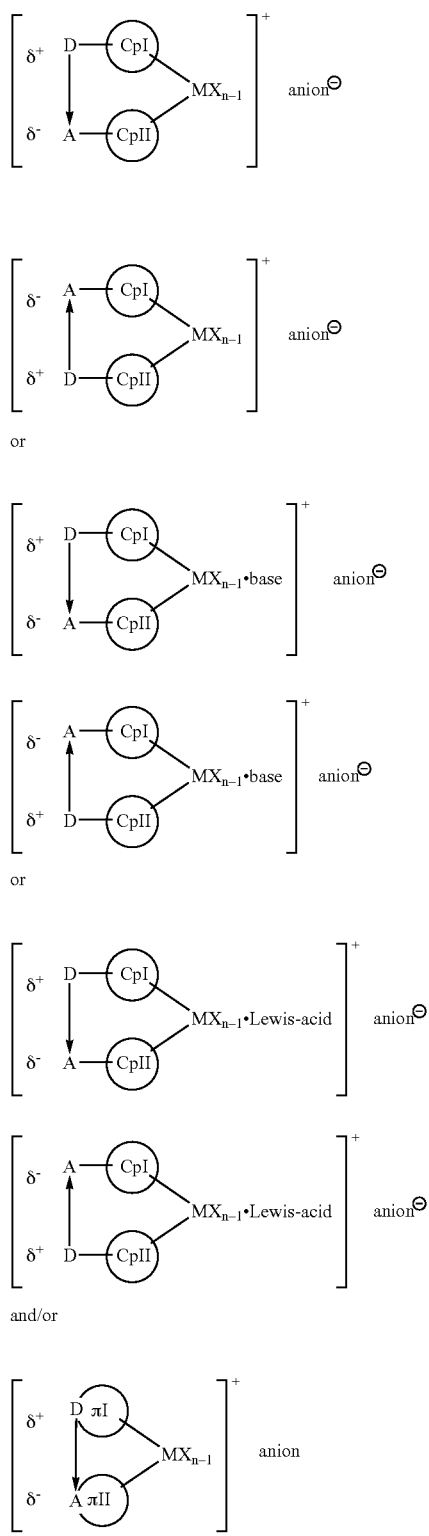

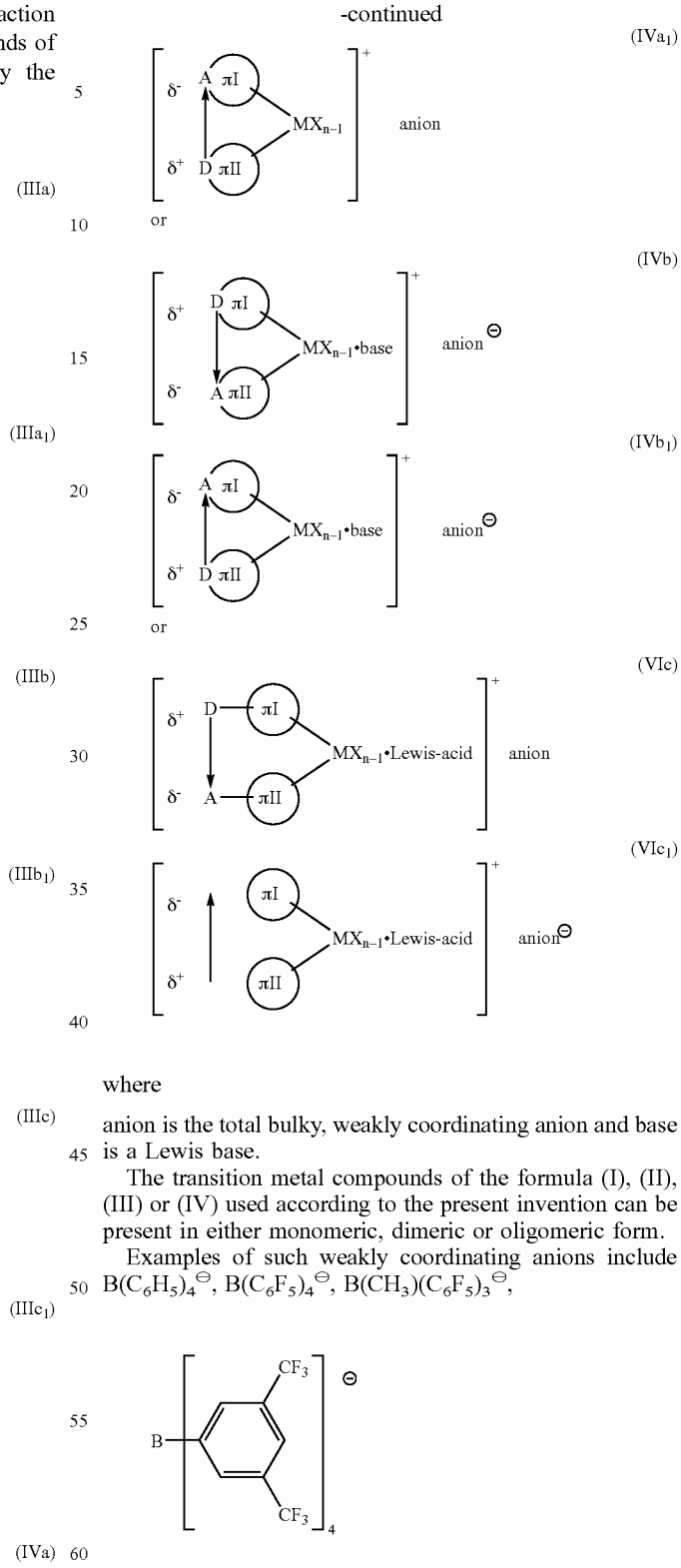

where anion is the total bulky, weakly coordinating anion and base is a Lewis base.

The transition metal compounds of the formula (I), (II), (III) or (IV) used according to the present invention can be present in either monomeric, dimeric or oligomeric form.

Examples of such weakly coordinating anions include $B(C_6H_5)_4^\ominus$, $B(C_6F_5)_4^\ominus$, $B(CH_3)(C_6F_5)_3^\ominus$,

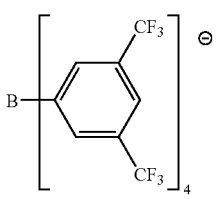

or sulphonates such as tosylate or triflate, tetrafluoroborates, hexafluorophosphates or hexafluoroantimonates, perchlorates and also bulky cluster molecule anions of the carborane type, for example $C_2B_9H_{12}^\ominus$ or $CB_{11}H_{12}^\ominus$, and substituted or unsubstituted cyclopentadienyl, indenyl and fluorenyl anions. Possible substituents are those which have been described for CpI and CpII. When such anions are present, π complexes can act as highly effective polymerization catalysts even in the absence of aluminoxane. This is the case when an X ligand is an alkyl or benzyl group. However, it can also be advantageous to use such π complexes having bulky anions in combination with aluminum alkyls such as $(CH_3)_3Al$, $(C_2H_5)_3Al$, (n-/i-propyl)$_3$Al, (n-/t-butyl)$_3$Al, (i-butyl)$_3$Al, the isomer pentyl, hexyl or octyl aluminum alkyls, or lithium alkyls such as methyl-Li, benzyl-Li, butyl-Li or the corresponding organomagnesium compounds such as Grignard compounds or organotin compounds. Such metal alkyls transfer alkyl groups to the central metal and also scavenge water or catalyst poisons from the reaction medium or monomers in polymerization reactions. Examples of aluminum or boron compounds from which such anions can be derived include:
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,5-trimethylanilinium) tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate,
N,N-dimethyl(2,4,6-trimethylanilinium) tetrakis(2,3,4,6-tetrafluorophenyl)borate;
dialkylammonium salts such as:
di(i-propyl)ammonium tetrakis(pentafluorophenyl)borate and
dicyclohexylammonium tetrakis(pentafluorophenyl)borate;
trisubstituted phosphonium salts such as:
triphenylphosphonium tetrakis(pentafluorophenyl)borate,
tri(o-tolyl)phosphonium tetrakis(pentafluorophenyl)borate,
tri(2,6-dimethylphenyl)phosphonium tetrakis(pentafluorophenyl)borate,
tritolylmethyl tetrakis(pentafluorophenyl)borate,
triphenylmethyl tetraphenylborate (trityl tetraphenylborate),
trityl tetrakis(pentafluorophenyl)borate,
silver tetrafluoroborate,
tris(pentafluorophenyl)borane,
tris(trifluoromethyl)borane and also the analogous aluminum compounds.

The transition metal compounds or metallocene compounds used according to the invention can be employed as pure materials in isolated form for the (co)polymerization. However, it is also possible for them to be generated and used "in situ" in the (co)polymerization reactor in a manner known to those skilled in the art.

Further cocatalysts are, for example, aluminoxane compounds. These are, for the purposes of the present invention, compounds of the formula (V)

where
R is $C_1$–$C_{20}$-alkyl, $C_6$–$C_{12}$-aryl or benzyl and
n is an integer from 1 to 50, preferably from 10 to 35.

It is likewise possible to use a mixture of various aluminoxanes or a mixture of their precursors (aluminum alkyls or alkylaluminum halides) in combination with water (in gaseous, liquid, solid or bound form, for instance as water of crystallization). The water can also be introduced as (residual) moisture in the polymerization medium, the monomer or a support such as silica gel or aluminosilicate.

The bonds projecting from the square bracket of formula (V) bear R groups or $AlR_2$ groups or HO groups at the ends of the oligomeric aluminoxane chain. Such aluminoxanes are generally in the form of a mixture of a plurality of such molecules having different chain lengths. Close examination has also revealed aluminoxanes having cyclic or cage-like structures. Aluminoxanes are commercial products. In the specific case of R=$CH_3$, the compound is methylaluminoxane (MAO).

The transition metal compound/compounds and/or the cocatalyst/cocatalysts can be used either as such in homogeneous form or individually or together in heterogeneous form on supports. The support material can be inorganic or organic in nature, e.g. silica gel, $B_2O_3$, $Al_2O_3$, $MgCl_2$, cellulose derivatives, starch and polymers or else sheet silicates such as montmorillonite.

Support materials are preferably pretreated thermally and/or chemically to set a defined water content or OH group concentration or to keep them as low as possible. An example of chemical pretreatment is the reaction of the support with an aluminum alkyl. Inorganic supports are frequently heated at from 100° C. to 1000° C. for from 1 to 100 hours before use. The surface area of such inorganic supports, preferably silica ($SiO_2$), is in the range from 10 to 1000 m$^2$/g, preferably from 100 to 800 m$^2$/g. The particle diameter is in the range from 0.1 to 500 microns (μm), preferably from 10 to 200 μm.

The ratio of cocatalyst to catalyst is in the range ≦100 000:1, preferably ≦10 000:1, more preferably ≦1000:1, most preferably ≦300:1.

Examples of olefins, i-olefins, cycloolefins, alkynes and diolefins which can be reacted in the homopolymerization or copolymerization include ethylene, propylene, 1-butene, i-butene, 1-pentene, 1-hexene, 1-octene, 3-methyl-1-butene, 4-methyl-1-pentene, 4-methyl-1-hexene, 1,3-butadiene, isoprene, 1,4-hexadiene, 1,5-hexadiene and 1,6-octadiene or methyloctadienes, chloroprene, acetylene, methylacetylene. α-Olefins having 20 and more carbon atoms are also possible. Even vinyl-terminated macromolecules can be incorporated as comonomers and thus lead to long-chain branching. The long-chain-branched polymers are presumably formed by in-situ copolymerization of the monomers used with macromolecules which have already been formed.

Such side chains can then reach chain lengths comparable with the length of the main chain.

Apart from the dienes mentioned, further open-chain, monocyclic and polycyclic dienes include the following: 5-methyl-1,4-hexadiene, 3,7-dimethyl1,6-octadiene; cyclopentadiene, 1,4-hexadiene, 1,5-cyclooctadiene; tetrahydroindene, methyltetrahydroindene, dicyclopentadiene, divinylbenzene, bicycle[2.2.1]hepta-2,5-diene, norbornenes bearing substituents such as alkenyl, alkylidene, cycloalkenyl, cycloalkylidene, e.g. 5-methylene-2-norbornene (MNB), 5-ethylidene-2-norbornene, 5-isopropylidene-2-norbornene, 5-vinyl-2-norbornene; allylcyclohexene, vinylcyclohexene.

Further preferred monomers in addition to those mentioned above include: dicyclopentadiene, 1,4-hexadiene, 5-methyl-2-norbornene, 5-ethylidene-2-norbornene and 5-vinyl-2-norbornene. It is, of course, also possible to use mixtures.

Futhermore, a cyclizing polymerization of α,ω-diolefins can be carried out; for example, 1,5-hexadiene can be polymerized to form poly(methylene-1,3-cyclopentane):

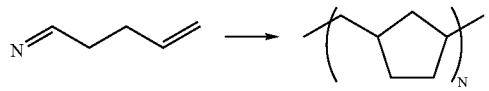

α,ω-Diolefins can also be used for producing long-chain branches. Examples of such dienes are 1,5-hexadiene, 1,7-octadiene, 1,9-decadiene. The side chains formed reach chain lengths comparable with the main chain.

If trialkylsilyl-substituted α,ω-diolefins are employed, a functional group can subsequently be introduced by polymer-analogous reaction.

Furthermore, the olefins and diolefins can be substituted, for example by phenyl, substituted phenyl, halogen, hydroxyl, boranyl, diorganoamino, an esterified carboxyl group, an acid anhydride group; examples of compounds of this type include styrene, methylstyrene, divinylbenzene, chlorostyrene, fluorostyrene, indene, 4-vinylbiphenyl, vinylfluorene, vinylanthracene, methyl methacrylate, ethyl acrylate, vinylsilane, trimethylallylsilane, vinyl chloride, vinylidene chloride, tetrafluoroethylene, isobutylene, vinylcarbazole, vinylpyrrolidone, acrylonitrile, vinyl ethers and vinyl esters, undecenol or vinylnorbornene.

Furthermore, ring-opening polyadditions, for instance of lactones such as ε-caprolactone or δ-valerolactone, of lactams such as ε-caprolactam or of epoxides such as ethylene oxide or propylene oxide or of other cyclic ethers such as tetrahydrofuran, are also possible according to the present invention.

Cycloolefins which can be used are described in the patent applications WO-98/01483 and WO-98/01484 (e.g. in WO 98/01484, page 31, line 20, to page 34, line 8).

Preferred monomers include: ethylene, propylene, butene, hexene, octene, 1,5-hexadiene, 1,6-octadiene, cycloolefins, methyl methacrylate, ε-caprolactone, δ-valerolactone and acetylene. It is possible to carry out the abovementioned (co)polymerizations in the presence of hydrogen, for instance to adjust the molar mass.

Elastomers which can be prepared according to the present invention include, for example, ethylene-propylene copolymer (EPM), ethylene-butene copolymer (EBM), ethylene-pentene copolymer, ethylene-hexene copolymer (EHM), ethylene-heptene copolymer, ethylene-octene copolymer (EOM), ethylenepropylene-butene copolymer, atactic polypropylene (aPP), propylene-hexene copolymers, propylene-octene copolymers, ethylene-vinyl acetate copolymers containing no crosslinker monomers and also ethylene-propylene-diene copolymer (EPDM), ethylene-butene-diene copolymer (EBDM), ethylene-hexene (or octene)-diene copolymer (EHDM or EODM), aPP without or with crosslinker monomers such as ethylidenenorbornene; the proportion of crosslinker monomers, e.g. the diene, is up to 20% by weight of all comonomers, e.g. from 0.1 to 20% by weight, preferably from 1 to 12% by weight, particular preferably from 2 to 8% by weight. Preferred elastomers are EPM, EHM, EHDM, aPP, atactic polypropylene having a relatively high isotactic or syndiotactic content and EPDM.

Such elastomers have good elasticity even at low temperatures due to a largely amorphous structure (no crystallinity or low crystallinity, i.e. a degree of crystallinity of less than 25%, preferably less than 15%, more preferably less than 10%, measured by methods known to those skilled in the art) having a low glass transition temperature $T_g$. The $T_g$ is preferably 0° C. or below, more preferably below 0° C. The elastomers have mean viscosity molar masses $M_\eta$ of greater than or equal to 50 kg/mol, preferably greater than 200 kg/mol, more preferably greater than 500 kg/mol. According to the present invention, it is possible to achieve the high molar masses mentioned together with a uniform distribution of the comonomers. In the case of dienes or other monomers capable of crosslinking, good crosslinking in the vulcanization is made possible by the uniform distribution. Furthermore, it is possible to obtain long-chain-branched products in which the length of the side chains can reach the length of the main chain.

The homopolymerizations or copolymerizations or polyadditions carried out using the novel, supported or unsupported transition metal compounds having a donor-acceptor interaction are carried out adiabatically or isothermally in the temperature and pressure ranges indicated. The process of the present invention is carried out in the bulk, solution, slurry or gas phase. The solution phase or the slurry phase can be formed by the comonomers alone, e.g. without use of an additional solvent. If a solvent is used, possible solvents are inert solvents, for example aliphatic or cycloaliphatic hydrocarbons, petroleum spirit or diesel oil fractions (if appropriate after hydrogenation), toluene, chlorobenzene, o-dichlorobenzene or chloronaphthalene. In the case of solvents having a low boiling point, the liquid phase can be maintained by application of a sufficient reaction pressure; such relationships are known to those skilled in the art. According to the invention, the reaction is carried out in one or more reactors or reaction zones, e.g. in reactor cascades, and different polymerization conditions can be used. It is possible to employ high-pressure processes in autoclaves or tube reactors, solution processes and also bulk polymerization processes, processes in the slurry phase in stirred reactors or loop reactors and processes in the gas phase, with the pressures for the slurry-, solution- and gas-phase processes not going above 100 bar. Such polymerizations can also be carried out in the presence of hydrogen. All these processes have been known for a long time and a person skilled in the art will be familiar with them.

The novel, supported or unsupported transition metal compounds having a donor-acceptor interaction make it possible to achieve, by means of the donor-acceptor bridge, a defined opening of the two cyclopentadienyl skeletons or the two ligands in the manner of a beak, with not only a high activity but also a high molar mass, a controlled molecular weight distribution and a uniform incorporation of comonomers being possible. As a result of this defined beak-like opening, there is also room for bulky comonomers. A high uniformity in the molecular weight distribution, namely $M_w/M_n<4$, preferably <3, also results from the uniform and defined site of the polymerization preceding by insertion (single site catalyst).

The D/A structure can give extra stabilization of the catalysts up to high temperatures, so that the catalysts can also be used in the relatively high and high temperature ranges from 50° C. to 80° C. and from 81° C. to 250° C. The possible thermal dissociation of the donor-acceptor bond is reversible and leads as a result of this self-organization process and self-repair mechanism to particularly valuable catalyst properties. The thermal dissociation makes it possible, for example, to achieve a targeted broadening of the molecular weight distribution or formation of bimodal or multimodal distributions, as a result of which the polymers become more readily processable. Preferably, the catalysts of the present invention make it possible to achieve defect-free growth of the polymer chains to extremely high molar masses.

regiospecific and stereospecific (isotactic, syndiotactic) polymerization of suitable monomers, but in the upper part of the abovementioned temperature range produce increasingly unspecific (atactic) linking of the monomer units of the same monomer. This phenomenon has not been examined fully, but could be in agreement with the observation that coordinate bonds which are superimposed on an ionic bond, e.g. the donor-acceptor bonds in the metallocene compounds of the invention, display increasing reversibility at higher temperature. Thus, for example, it has been observed in the case of ethylene-propylene copolymerization that when the same amount of each comonomer is made available, a copolymer having a high propylene content is formed at a low polymerization temperature and the propylene content decreases with rising polymerization temperature until finally polymers comprising predominantly ethylene are formed at high temperature.

The reversible dissociation and association of the D/A structure and the relative rotation of the ligands, for example the Cp units, which is made possible as a result can be shown schematically as follows:

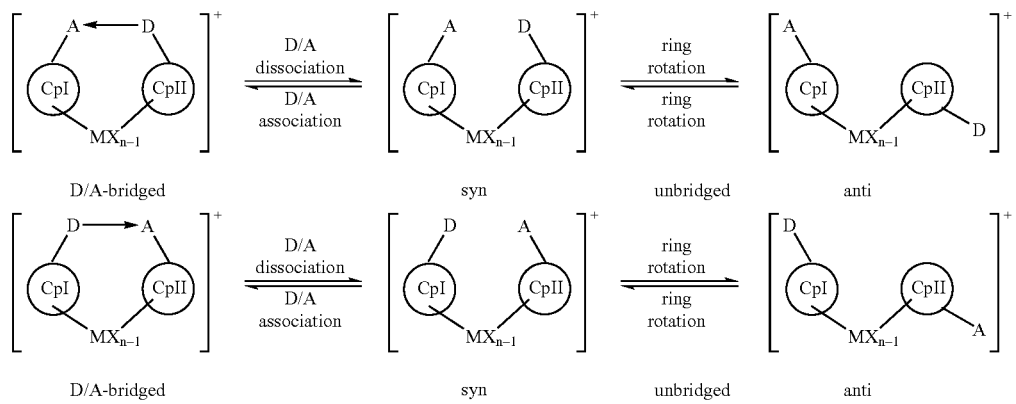

This also applies to elastomeric homopolymers and copolymers.

Although the molar mass is reduced by increasing the polymerization temperature within a wide temperature range, this occurs without an appreciable reduction in activity and without departure from the overall range of industrially interesting high molar masses and low glass transition temperatures.

Furthermore, it has been observed that transition metal compounds according to the present invention having a donor-acceptor interaction of suitable symmetry effect A further valuable property of the novel supported catalysts having a donor-acceptor interaction is the possibility of self-activation and thus omission of expensive cocatalysts. Here, the acceptor atom A in the open form of the D/A metallocene compound binds an X ligand to form a zwitterionic structure and thus generates a positive charge on the transition metal, while the acceptor atom A acquires a negative charge. Such self-activation can occur intramolecularly or intermolecularly. This can be illustrated using the linkage of two X ligands to form a chelating ligand, namely a butadienediyl derivative, as an example:

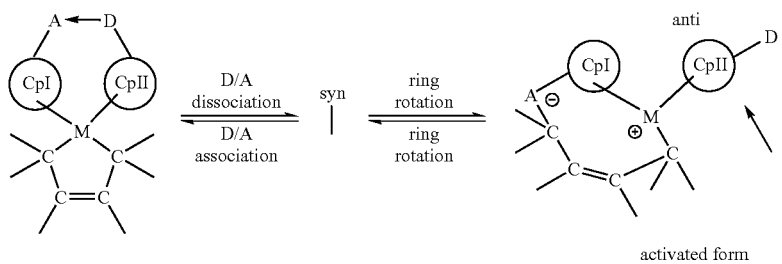

-continued

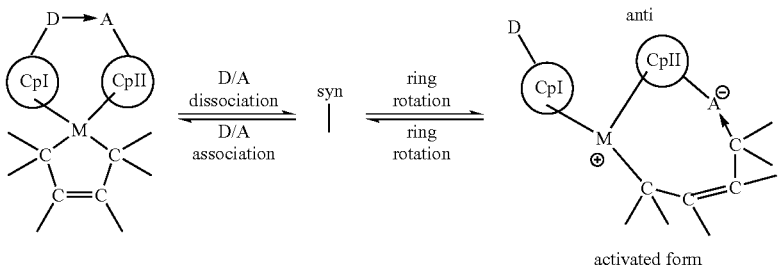

activated form

The bonding position between the transition metal M and H or a substituted or unsubstituted C, for instance the C of the butadienediyl dianion shown in the example which is still bound, is then the site of olefin insertion in the polymerization.

Furthermore, the novel, supported or unsupported, transition metal compounds having a donor-acceptor interaction are suitable for preparing both thermoplastic polymers and elastomeric polymers by the various processes mentioned above, with both highly crystalline polymers having an optimized melting range and amorphous polymers having an optimized glass transition temperature being obtainable. The polymers having a low glass transition temperature below 0° C. and a high melting point of >80° C. in the same material which can be prepared in this way are of interest.

The polymers which can be prepared are extremely useful for producing shaped bodies of all types, in particular films, tubing for, inter alia, medical applications, profiles, plates, optical data storage media, cable sheathing and extrudates, for surgical implants, running surface materials for skis, impact modifiers for thermoplastics, e.g. for automobile bumpers, for door and windowsills, dental braces, etc.

The following examples illustrate the invention.

EXAMPLE 1

Fluorenyllithium Li[flu]Li($C_{13}H_9$)

A solution of fluorene (11.09 g, 66.74 mmol) in 300 ml of dry pentane was admixed at −70° C. with BuLi (28.0 ml of a 2.5 molar solution, 70.0 mmol). The pale yellow solution obtained was stirred at room temperature under an argon atmosphere for 16 hours and then refluxed for 24 hours. The orange-yellow solution was filtered by means of a needle and the yellow residue was washed with pentane (2×100 ml, in each case for about 15 minutes under reflux) and filtered. The orange-yellow powder was dried to constant weight under a dynamic vacuum, giving 9.10 g (79.2%) of loose orange powder as pure fluorenyllithium product.

$^1$H-NMR: (400.13 MHz, THF-$d_8$), δ 7.86 (d, J=7.53 Hz, 2H), 7.25 (d, J=7.96 Hz, 2H), 6.75 (td, $J_1$=6.65 Hz, $J_2$=1.22 Hz, 2H), 6.37 (t, J=7.64 Hz, 2H), 5.88 (s, 1H)

EXAMPLE 2

9-Diethylphosphinofluorenyllithium Li[$Et_2$P-flu]Li [9-($C_2H_5$)$_2$P—($C_{13}H_8$)]

A suspension of fluorenyllithium, ($C_{13}H_9$)Li, (2.728 g, 15.85 mmol) in 30 ml of dry pentane was admixed at −70° C. with a solution of chlorodiethylphosphine, ClPEt$_2$, (1.974 g, 15.85 mmol) in 25 ml of pentane. The mixture was stirred briefly at −70° C. and then reacted at room temperature for 6 hours. The yellow suspension was filtered and the filtrate was freed of volatile components under reduced pressure, leaving 3.49 g (86.6%) of an orange oil which, according to 1-H- and 31-P-NMR spectroscopy, was 9-diethylphosphinofluorene. The resulting compound (9-diethylphosphinofluorene, 3.388 g, 13.3 mmol) was diluted with 45 ml of dry pentane and cooled to 0° C. The cooled solution was admixed with BuLi (5.4 ml of a 2.5 molar solution, 13.5 mmol) and stirred briefly. The mixture was stirred for another 4.5 hours at room temperature with occasional heating by means of a hairdryer, resulting in a few loose orange precipitates. The reaction mixture was filtered with the aid of a needle and the solid was washed with pentane (2×5 ml) and dried under reduced pressure, leaving an orange solid which, according to 1-H- and 31-P-NMR spectroscopy, was 9-diethylphosphinofluorenyllithium.

NMR: $^1$H (400.13 MHz, THF-$d_8$), δ 7.79 (d, J=7.5 Hz, 2H), 7.68 (d, J=8.2 Hz, 2H), 6.76 (dt, $J_1$=6.8 Hz, $J_2$=1.3 Hz, 2H), 6.41 (dt, $J_1$=6.8 Hz, $J_2$=0.8 Hz, 2H=, 2.08 (m, 2H), 1.82 (m, 2H), 0.90 (m, 6H). $^{31}$P (161.9 MHz, THF-$d_8$), δ −40.4 (singlet).

EXAMPLE 3

Diphenylbromoborane (diphenylboron bromide) Ph$_2$BBr ($C_6H_5$)$_2$BBr 43.3 g (101.4 mmol) of tetraphenyltin SnPh$_4$ were placed under argon in a 500 ml two-neck flask and cooled to −70° C. At −70° C., 50.8 g (202.8 mmol) of BBr$_3$ were added slowly by means of a syringe while stirring. At 0° C., a strongly exothermic reaction occurred, resulting in a brief rise in the internal temperature to about 40° C. The mixture was stirred at room temperature for 2 hours, then heated to 220° C. and maintained at this temperature for 2 hours. The product Ph$_2$BBr was purified by fractional vacuum distillation.

B.p.$_{0.1}$ 90° C.–95° C. Yield: 39.22 g (78.9% of theory). $^{11}$B-NMR (128.4 MHz, $d_8$-toluene) δ +66.1 (singlet).

EXAMPLE 4

Diphenylboranyltrimethylsilylcyclopentadiene Ph$_2$B-cp-SiMe$_3$ ($C_6H_5$)$_2$B—($C_5H_4$)—Si(CH$_3$)$_3$ 9.69 g (70.1 mmol) of trimethylsilylcyclopentadiene (from Fluka) and 600 ml of n-pentane were placed under argon in a 1 l two-neck flask at −50° C. 43.8 ml (70.1 mmol) of butyllithium (BuLi) 1.6 molar in n-hexane were added dropwise. After the addition of BuLi was complete, the yellow suspension was stirred overnight at room temperature. It was subsequently cooled to −20° C. and a solution of 17.16 g (70.1 mmol) of Ph$_2$BBr in 50 ml of n-pentane was added dropwise at −20° C. The suspension was stirred overnight at room temperature, filtered through a D3 frit and the filtrate was evaporated to dryness. The product is a yellow oil which, according to NMR, is an isomer mixture.

Yield: 17.5 g (82.8%).

EXAMPLE 5

1-Diphenylboranylcyclopentadienylzirconium trichloride [$Ph_2B(cp)ZrCl_3$] [$(C_6H_5)_2B(C_5H_4)ZrCl_3$]

24.8 g (106.5 mmol) of zirconium tetrachloride and 150 ml of toluene were placed under argon in a 0.5 l two-neck flask. The white suspension was cooled to −20° C. and a solution of 30.68 g (101.4 mmol) of diphenylboranyltrimethylsilylcyclopentadiene in 150 ml of toluene was added. The brown suspension was stirred at room temperature for 24 hours and filtered through a D3 frit. The filtrate was evaporated to dryness under reduced pressure. The brown residue was stirred a number of times with n-hexane, giving a brown powder. This was dried to constant weight under reduced pressure.

Yield: 26.26 g (60.7% of theory).

EXAMPLE 6

9-Diethylphosphinofluorenyl-1-diphenylboranylcyclopentadienylzirconium dichloride [$(flu)Et_2PBPh_2(cp)ZrCl_2$], [$(C_{13}H_8)(C_2H_5)_2PB(C_6H_5)_2(C_5H_4)ZrCl_2$]

0.63 g (2.4 mmol) of Li[$Et_2P$-flu] together with 60 ml of toluene were placed under argon in a Schlenk tube at room temperature, and a solution of 1.03 g (2.4 mmol) of $Ph_2B(cp)ZrCl_3$ in 30 ml of toluene was slowly added dropwise at room temperature. The suspension changed colour from yellow to brown. After 4 hours at room temperature, the suspension was filtered and the filtrate was evaporated to dryness and stirred 3 times with 15 ml of pentane. The light-brown residue was dried to constant weight.

Yield: 1.04 g (67% of theory). NMR: $^1H$ (400.13 MHz, $CD_2Cl_2$) δ +8.23 (d, 9 Hz, 2H,flu), +7.84 (d, 9 Hz, 2H,flu), +7.67 (pseudo-t, 7.7 Hz, 2H,flu), +7.4 (m, Ph), +7.35 (pseudo-t, 7.6 Hz, 2H,flu), +7.26 (m, Ph), +6.65 (m, 2H, cp), +6.25 (pseudo-t, 2.5 Hz, 2H, cp), +2.54 (m, 4H, $CH_2$), +1.04 (m, 6H, $CH_3$). $^{11}B$ (128.38 MHz, $CD_2Cl_2$) δ −4.6 (broadened singlet). $^{31}P$ (161.98 MHz, $CD_2Cl_2$) δ +30.0 (broadened singlet).

EXAMPLE 7

Polymerization of Ethene 100 ml of dry toluene which had been distilled under inert gas were placed in a dry, oxygen-free 300 ml V4A steel autoclave and the catalyst was added at 40° C. by means of a syringe. The catalyst employed comprised $5\times10^{-8}$ mol of [$(flu)Et_2PBPh_2(cp)ZrCl_2$] in 0.33 ml of a 10% strength solution of MAO in toluene (0.5 mmol of Al). A constant pressure of 10 bar was set by means of ethene. The polymerization proceeded in the temperature range from 40° C. to 48° C. and was stopped after 30 minutes. The polyethylene formed was stirred with ethanol/hydrochloric acid 90/10, filtered, washed with ethanol and dried to constant weight at 80° C. in a vacuum drying oven.

| | |
|---|---|
| Polymer yield: | 1.0 g |
| Catalyst activity: | 40.0 tonnes of PE per mole of Zr and hour |
| Limiting viscosity in ortho-dichlorobenzene at 140° C.: | [η] = 20.33 dl/g |
| corresponding to a calculated mean molar mass $M_\eta$: derived from [η] = k · $M^\alpha$ where k = 4.96 · $10^{-4}$ α = 0.700 | 3887 kg/mol |
| DSC: (1st heating) | |
| melting point: | $T_m$ = 145° C. |
| enthalpy of fusion: | $H_m$ = 256 J/g |
| DSC: (2nd heating) | |
| melting point: | $T_m$ = 138° C. |
| enthalpy of fusion: | $H_m$ = 133 J/g |

EXAMPLE 8

Polymerization of Ethene 100 ml of dry toluene which had been distilled under inert gas were placed in a dry, oxygen-free 300 ml V4A steel autoclave and the catalyst was added at 80° C. by means of a syringe. The catalyst employed comprised $7.5\times10^{-8}$ mol of [$(flu)Et_2PBEt_2(cp)ZrCl_2$] in 0.5 ml of a 10% strength solution of MAO in toluene (0.75 mmol of Al). A constant pressure of 10 bar was set by means of ethene. The polymerization proceeded in the temperature range from 80° C. to 86° C. and was stopped after 30 minutes. The polyethylene formed was stirred with ethanol/hydrochloric acid 90/10, filtered, washed with ethanol and dried to constant weight at 80° C. in a vacuum drying oven.

| | |
|---|---|
| Polymer yield: | 1.2 g |
| Catalyst activity: | 32.0 tonnes of PE per mole of Zr and hour |
| Limiting viscosity in ortho-dichlorobenzene at 140° C.: | [η] = 13.84 dl/g |
| corresponding to a calculated mean molar mass $M_\eta$: derived from [η] = k · $M^\alpha$ where k = 4.96 · $10^{-4}$ α = 0.700 | 2244 kg/mol |
| DSC: (1st heating) | |
| melting point: | $T_m$ = 145° C. |
| enthalpy of fusion: | $H_m$ = 256 J/g |
| DSC: (2nd heating) | |
| melting point: | $T_m$ = 138° C. |
| enthalpy of fusion: | $H_m$ = 149 J/g |

EXAMPLE 9

Copolymerization of Ethene and Hexene 100 g of dry 1-hexene which had been distilled under inert gas were placed in a dry, oxygen-free 300 ml V4A steel autoclave. At an internal temperature of 40° C., the pressure was set to 15 bar by means of ethene. The catalyst employed comprised $2.5\times10^{-7}$ mol of [$(flu)Et_2PBPh_2(cp)ZrCl_2$] and 1.65 ml of a 10% strength solution of MAO in toluene (2.5 mmol of Al). The catalyst was added via a pressure lock. The polymerization proceeded in the temperature range from 40° C. to 45° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 13.7 g |
| Catalyst activity: | 109.6 tonnes of rubber per mole of Zr and hour |
| NMR: | |
| Hexene: | 42% by weight |
| Ethene: | 58% by weight |
| Limiting viscosity in ortho-dichlorobenzene at 140° C.: | [η] = 3.74 dl/g |
| DSC: (2nd heating) | |
| glass transition temperature broad melting range from −55° C. to +125° C. | $T_g$ = −63° C. |
| enthalpy of fusion: | $H_m$ = 29 J/g |

EXAMPLE 10

Polymerization of Propene

About 1 mol of propene was placed in a dry, oxygen-free 300 ml V4A steel autoclave and the polymerization was started in bulk at 20° C. by addition of catalyst via a pressure lock. The catalyst employed comprised $1 \times 10^{-6}$ mol of [(flu)Et$_2$PBPh$_2$(cp)ZrCl$_2$] in 6.6 ml of a 10% strength solution of MAO in toluene (10 mmol of Al). The polymerization proceeded in the temperature range from 20° C. to 22° C. and was stopped after 30 minutes. The elastomeric polypropene formed was stirred with ethanol/hydrochloric acid 90/10, filtered, washed with ethanol and dried to constant weight at 80° C. in a vacuum drying oven.

| | |
|---|---|
| Polymer yield: | 7.0 g |
| Catalyst activity: | 14.0 tonnes of PP per mole of Zr and hour |
| NMR (triad analysis): | |
| 5% isotactic | (mm) |
| 21% atactic | (mr/rm) |
| 74% syndiotactic | (rr) |
| Limiting viscosity in ortho-dichlorobenzene at 140° C.: | [η] = 3.23 dl/g |
| corresponding to a calculated mean molar mass $M_\eta$: derived from [η] = k · $M^\alpha$ where k = 1.02 · $10^{-4}$ α = 0.780 | 588 kg/mol |
| DSC: (1st heating) partially crystalline | |
| glass transition temperature: | $T_g$ = +1° C. |
| melting point: | $T_m$ = 87° C. |
| DSC: (2nd heating) amorphous | |
| glass transition temperature: | $T_g$ = −1° C. |

EXAMPLE 11

Copolymerization of Ethene and Propene 100 m of dry toluene which had been distilled under inert gas and 10 g of propene were placed in a dry, oxygen-free 300 ml V4A steel autoclave. At an internal temperature of 40° C., the pressure was increased from 3 bar to 5 bar by means of ethene. The catalyst employed comprised $1 \times 10^{-7}$ mol of [(flu)Et$_2$PBPh$_2$(cp)ZrCl$_2$] and 1.65 ml of a 10% strength solution of MAO in toluene (1 mmol of Al). The catalyst was added via a pressure lock and the pressure was increased from 5 bar to 7 bar. The polymerization proceeded in the temperature range from 40° C. to 45° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 4.1 g |
| Catalyst activity: | 82.0 tonnes of EP rubber per mole of Zr and hour |
| FTIR: | |
| Propene: | 57% by weight |
| Ethene: | 43% by weight |
| Limiting viscosity in ortho-dichlorobenzene at 140° C.: | [η] = 6.04 dl/g |
| corresponding to a calculated mean molar mass $M_\eta$: derived from [η] = k · $M^\alpha$ where k = 4.00 · $10^{-4}$ dl/g α = 0.710 | 769 kg/mol |
| DSC: (2nd heating) | |
| glass transition temperature: | $T_g$ = −54° C. |
| melting point: | $T_m$ = −20° C. |
| enthalpy of fusion: | $H_m$ = 8 J/g |

Polymerizations carried out analogously at above 45° C. also gave very high molecular weight EP rubbers, e.g. at a polymerization temperature $T_p$ of from 60° C. to 63° C., a limiting viscosity η in ODCB at 140° C. of 4.01 dl/g was measured, and at $T_p$=80° C.–81° C., a η value of 2.45 dl/g was determined.

EXAMPLE 12

Copolymerization of Ethene and Propene 100 ml of dry toluene which had been distilled under inert gas, 10 g of propene and 0.35 mmol of a 1 molar solution of triisobutylaluminum (TIBA) in toluene were placed in a dry, oxygen-free 300 ml V4A steel autoclave. At an internal temperature of 40° C., the pressure was increased from 3 bar to 5 bar by means of ethene. The catalyst employed comprised $2.5 \times 10^{-7}$ mol of [(flu)Et$_2$PBPh$_2$(cp)ZrCl$_2$] in 0.25 ml of a 1 molar solution of TIBA in toluene (25 μmol of Al) and 1 μmol of N,N-dimethylanilinium tetrakispentafluorophenylborate in chlorobenzene (1 μmol/1 ml). The catalyst was added via a pressure lock and the pressure was increased from 5 bar to 7 bar. The polymerization proceeded in the temperature range 40°–42° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 2.0 g |
| Catalyst activity: | 16.0 tonnes of EP rubber per mole of Zr and hour |
| FTIR: | |
| Propene: | 31% by weight |
| Ethene: | 69% by weight |
| Limiting viscosity in ortho-dichlorobenzene at 140° C.: | [η] = 4.71 dl/g |
| corresponding to a calculated mean molar mass $M_\eta$: derived from [η] = k · $M^\alpha$ where k = 4.00 · $10^{-4}$ α = 0.710 | 541 kg/mol |
| DSC: (2nd heating) partially crystalline copolymer | |
| glass transition temperature: | $T_g$ = −47° C. |
| melting point: | $T_m$ = 81° C. |
| enthalpy of fusion: | $H_m$ = 57 J/g |

EXAMPLE 13

Copolymerization of Ethene and Propene 100 ml of dry toluene which had been distilled under inert gas and 10 g of propene were placed in a dry, oxygen-free 300 ml V4A steel autoclave. At an internal temperature of 60° C., the pressure was increased from 4 bar to 6 bar by means of ethene. The catalyst employed comprised $2 \times 10^{-7}$ mol of [(flu)Et$_2$PBEt$_2$(cp)ZrCl$_2$] and 1.32 ml of a 10% strength solution of MAO in toluene (2 mmol of Al). The catalyst was added via a pressure lock and the pressure was increased from 6 bar to 8 bar. The polymerization proceeded in the temperature range from 60° C. to 64° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 2.7 g |
| Catalyst activity: | 27.0 tonnes of EP rubber per mole of Zr and hour |
| FTIR: | |
| Propene: | 42% by weight |
| Ethene: | 58% by weight |
| Limiting viscosity in ortho-dichlorobenzene at 140° C.: | $[\eta]$ = 4.63 dl/g |
| corresponding to a calculated mean molar mass $M_\eta$: | 529 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -56°$ C. |
| melting point: | $T_m = -16°$ C./+87° C. |
| enthalpy of fusion: | $H_m$ = 17 J/g |

EXAMPLE 14

Copolymerization of Ethene and Propene 100 ml of dry toluene which had been distilled under inert gas and 10 g of propene were placed in a dry, oxygen-free 300 ml V4A steel autoclave. At an internal temperature of 40° C., the pressure was increased from 3 bar to 5 bar by means of ethene. The catalyst employed comprised $1 \times 10^{-7}$ mol of [(flu)Et$_2$PBPh$_2$(3-Mecp)ZrCl$_2$] and 0.66 ml of a 10% strength solution of MAO in toluene (1 mmol of Al). The catalyst was added via a pressure lock and the pressure was increased from 5 bar to 7 bar. The polymerization proceeded in the temperature range from 40° C. to 44° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 2.3 g |
| | 46.0 tonnes of EP rubber per mole of Zr and hour |
| FTIR: | |
| Propene: | 59% by weight |
| Ethene: | 41% by weight |
| Limiting viscosity in ortho-dichlorobenzene at 140° C.: | $[\eta]$ = 3.96 dl/g |
| corresponding to a calculated mean molar mass $M_\eta$: | 425 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -55°$ C./-46° C. |
| melting point: | $T_m = -15°$ C. |
| enthalpy of fusion: | $H_m$ = 1 J/g |

EXAMPLE 15

Copolymerization of Ethene and Propene 100 ml of dry toluene which had been distilled under inert gas and 10 g of propene were placed in a dry, oxygen-free 300 ml V4A steel autoclave. At an internal temperature of 40° C., the pressure was increased from 3 bar to 5 bar by means of ethene. The catalyst employed comprised $2 \times 10^{-7}$ mol of [(flu)Et$_2$PBPh$_2$(Phcp)ZrCl$_2$] and 1.32 ml of a 10% strength solution of MAO in toluene (2 mmol of Al). The catalyst was added via a pressure lock and the pressure was increased from 5 bar to 7 bar. The polymerization proceeded in the temperature range from 40° C. to 44° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 1.25 g |
| Catalyst activity: | 12.5 tonnes of EP rubber per mole of Zr and hour |
| FTIR: | |
| Propene: | 39% by weight |
| Ethene: | 61% by weight |
| Limiting viscosity in ortho-dichlorobenzene at 140° C.: | $[\eta]$ = 4.95 dl/g |
| corresponding to a calculated mean molar mass $M_\eta$: | 581 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -52°$ C. |
| broad melting range from | $-46°$ C. to +126° C. |
| enthalpy of fusion: | $H_m$ = 23 J/g |

EXAMPLE 16

Copolymerization of Ethene and Propene 100 ml of dry toluene which had been distilled under inert gas and 150 mg of montmorillonite K10 (from Fluka) which had been degassed under a high vacuum (10 minutes/$10^{-3}$ bar) and stored under argon together with 0.3 mmol of TIBA (1 m in toluene) were placed in a dry, oxygen-free 300 ml V4A steel autoclave and 10 g of propene were condensed in. At an internal temperature of 50° C., the pressure was increased from 3.5 bar to 5.5 bar by means of ethene. The catalyst employed comprised $5 \times 10^{-7}$ mol of [(flu)Et$_2$PBEt$_2$(cp)ZrCl$_2$] and 0.09 ml of a 10% strength solution of MAO in toluene (0.15 mmol of Al, Al/Zr=300). The catalyst was added via a pressure lock and the pressure was increased from 5.5 bar to 7.5 bar. The polymerization proceeded in the temperature range from 50° C. to 60° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 4.3 g |
| Catalyst activity: | 17.2 tonnes of EP rubber per mole of Zr and hour |
| FTIR: | |
| Propene: | 58% by weight |
| Ethene: | 42% by weight |
| Limiting viscosity in ortho-dichlorobenzene at 140° C.: | $[\eta] = 5.72$ dl/g |
| corresponding to a calculated mean molar mass $M_\eta$: | 712 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -55°$ C. |
| melting point: | $T_m = -27°$ C. |
| enthalpy of fusion: | $H_m = 11$ J/g |

EXAMPLE 17

Copolymerization of Ethene and Propene 100 ml of dry toluene which had been distilled under inert gas and 100 mg of montmorillonite K10 (from Fluka) which had been degassed under a high vacuum (10 minutes/$10^{-3}$ bar) and stored under argon together with 0.2 mmol of TIBA (1 m in toluene) were placed in a dry, oxygen-free 300 ml V4A steel autoclave and 10 g of propene were condensed in. At an internal temperature of 50° C., the pressure was increased from 3 bar to 4.5 bar by means of ethene. The catalyst employed comprised $5 \times 10^{-7}$ mol of [(flu)Et$_2$PBEt$_2$(cp)ZrCl$_2$] and 0.09 ml of a 10% strength solution of MAO in toluene (0.15 mmol of Al, Al/Zr=300). The catalyst was added via a pressure lock and the pressure was increased from 4.5 bar to 8 bar. The polymerization proceeded in the temperature range from 50° C. to 55° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 4.05 g |
| Catalyst activity: | 16.2 tonnes of EP rubber per mole of Zr and hour |
| FTIR: | |
| Propene: | 49% by weight |
| Ethene: | 51% by weight |
| Limiting viscosity in ortho-dichlorobenzene at 140° C.: | $[\eta] = 7.20$ dl/g |
| corresponding to a calculated mean molar mass $M_\eta$: | 985 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -54°$ C. |
| melting point: | $T_m = -10°$ C. |
| enthalpy of fusion: | $H_m = 11$ J/g |

EXAMPLE 18

Copolymerization of Ethene and Propene 100 ml of dry toluene which had been distilled under inert gas and 0.3 mmol of TIBA (1 m in toluene) were placed in a dry, oxygen-free 300 ml V4A steel autoclave. 10 g of propene were condensed in. At an internal temperature of 50° C., the pressure was increased from 3.5 bar to 5.5 bar by means of ethene. The catalyst employed comprised $5 \times 10^{-7}$ mol of [(flu)Et$_2$PBPh$_2$(cp)ZrCl$_2$] and 0.09 ml of a 10% strength solution of MAO in toluene (0.15 mmol of Al, Al/Zr=300).

The catalyst was added via a pressure lock and the pressure was increased from 5.5 bar to 7.5 bar. The polymerization proceeded in the temperature range from 50° C. to 54° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 4.0 g |
| Catalyst activity: | 16.0 tonnes of EP rubber per mole of Zr and hour |
| FTIR: | |
| Propene: | 59% by weight |
| Ethene: | 41% by weight |
| Limiting viscosity in ortho-dichlorobenzene at 140° C.: | $[\eta] = 5.53$ dl/g |
| corresponding to a calculated mean molar mass $M_\eta$: | 679 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -55°$ C. |
| melting point: | $T_m = -22°$ C. |
| enthalpy of fusion: | $H_m = 8$ J/g |

EXAMPLE 19

Copolymerization of Ethene and Propene 100 ml of dry toluene which had been distilled under inert gas and 150 mg of montmorillonite K10 (from Fluka) which had been degassed under a high vacuum (10 minutes/ $10^{-3}$ bar) and stored under argon together with 0.3 mmol of TIBA (1 m in toluene) were placed in a dry, oxygen-free 300 ml V4A steel autoclave. 10 g of propene were condensed in. At an internal temperature of 50° C., the pressure was increased from 3.5 bar to 5.5 bar by means of ethene. The catalyst employed comprised $5 \times 10^{-7}$ mol of [(flu)Et$_2$PBPh$_2$(cp)ZrCl$_2$] and 0.09 ml of a 10% strength solution of MAO in toluene (0.15 mmol of Al, Al/Zr=300). The catalyst was added via a pressure lock and the pressure was increased from 5.5 bar to 7.5 bar. The polymerization proceeded in the temperature range from 50° C. to 55° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 4.8 g |
| Catalyst activity: | 19.2 tonnes of EP rubber per mole of Zr and hour |
| FTIR: | |
| Propene: | 68% by weight |
| Ethene: | 32% by weight |
| Limiting viscosity in ortho-dichlorobenzene at 140° C.: | $[\eta] = 4.61$ dl/g |

-continued

| | |
|---|---|
| corresponding to a calculated mean molar mass $M_\eta$: | 526 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -42°$ C. |
| enthalpy of fusion: | $H_m = 0$ J/g |

EXAMPLE 20

Copolymerization of Ethene and Propene 100 ml of dry toluene which had been distilled under inert gas and 150 mg of montmorillonite K10 (from Fluka) which had been degassed under a high vacuum (10 minutes/ $10^{-3}$ bar) and stored under argon together with 0.2 mmol of TIBA (1 m in toluene) were placed in a dry, oxygen-free 300 ml V4A steel autoclave. 10 g of propene were condensed in. At an internal temperature of 50° C., the pressure was increased from 3.5 bar to 5.5 bar by means of ethene. The catalyst employed comprised $5\times10^{-7}$ mol of $[(flu)Et_2PBPh_2(cp)ZrCl_2]$ and 0.033 ml of a 10% strength solution of MAO in toluene (0.05 mmol of Al, Al/Zr=100). The catalyst was added via a pressure lock and the pressure was increased from 5.5 bar to 7.5 bar. The polymerization proceeded in the temperature range from 50° C. to 54° C. and was stopped after 30 minutes.

The polymer formed was stirred with ethanol/hydrochloric acid 90/10, filtered, washed with ethanol and dried to constant weight at 80° C. in a vacuum drying oven.

| | |
|---|---|
| Polymer yield: | 2.9 g |
| Catalyst activity: | 11.6 tonnes of EP rubber per mole of Zr and hour |
| FTIR: | |
| Propene: | 51% by weight |
| Ethene: | 49% by weight |
| Limiting viscosity in ortho-dichlorobenzene at 140° C.: | $[\eta] = 5.72$ dl/g |
| corresponding to a calculated mean molar mass $M_\eta$: | 712 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -55°$ C. |
| melting point: | $T_m = -22°$ C. |
| enthalpy of fusion: | $H_m = 4$ J/g |

EXAMPLE 21

Terpolymerization of Ethene, Propene and Ethylidenenorbornene 100 ml of dry toluene which had been distilled under inert gas, 0.3 mmol of TIBA (1 m in toluene) and 2 g of 5-ethylidene-2-norbornene and 10 g of propene were placed in a dry, oxygen-free 300 ml V4A steel autoclave. At an internal temperature of 50° C., the pressure was increased from 3.5 bar to 5.5 bar by means of ethene. The catalyst employed comprised $5\times10^{-7}$ mol of $[(flu)Et_2PBPh_2(cp)ZrCl_2]$ and 0.09 ml of a 10% strength solution of MAO in toluene (0.15 mmol of Al, Al/Zr=300). The catalyst was added via a pressure lock and the pressure was increased from 5.5 bar to 7.5 bar. The polymerization proceeded in the temperature range from 50° C. to 52° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 2.5 g |
| Catalyst activity: | 10.0 tonnes of EP rubber per mole of Zr and hour |
| FTIR: | |
| Propene: | 45% by weight |
| Ethene: | 51% by weight |
| ENB: | 4% by weight |
| Limiting viscosity in ortho-dichlorobenzene at 140° C.: | $[\eta] = 5.23$ dl/g |
| corresponding to a calculated mean molar mass $M_\eta$: | 679 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -52°$ C. |
| melting point: | $T_m = -19°$ C. |
| enthalpy of fusion: | $H_m = 6$ J/g |

EXAMPLE 22

Terpolymerization of Ethene, Propene and Ethylidenenorbornene 100 ml of dry toluene which had been distilled under inert gas, 150 mg of undried montmorillonite K 10 (from Fluka) which had been degassed in a high vacuum (10 minutes/ $10^{-3}$ bar) and stored under argon and also 0.3 mmol of TIBA (1 m in toluene) and 2 g of 5-ethylidene-2-norbornene and 10 g of propene were placed in a dry, oxygen-free 300 ml V4A steel autoclave. At an internal temperature of 50° C., the pressure was increased from 3.5 bar to 5.5 bar by means of ethene. The catalyst employed comprised $5\times10^{-7}$ mol of $[(flu)Et_2PBPh_2(cp)ZrCl_2]$ and 0.09 ml of a 10% strength solution of MAO in toluene (0.15 mmol of Al, Al/Zr=300). The catalyst was added via a pressure lock and the pressure was increased from 5.5 bar to 7.5 bar. The polymerization proceeded in the temperature range from 50° C. to 54° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 3.3 g |
| Catalyst activity: | 13.2 tonnes of EP rubber per mole of Zr and hour |
| FTIR: | |
| Propene: | 46% by weight |
| Ethene: | 50% by weight |
| ENB: | 4% by weight |
| Limiting viscosity in ortho-dichlorobenzene at 140° C.: | $[\eta] = 4.28$ dl/g |
| corresponding to a calculated mean molar mass $M_\eta$: | 474 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -51°$ C. |
| melting point: | $T_m = -13°$ C. |
| enthalpy of fusion: | $H_m = 6$ J/g |

EXAMPLE 23

Terpolymerization of Ethene, Propene and Ethylidenenorbornene 100 ml of dry pentane which had been distilled under inert gas, 10 g of propene and 1 g of 5-ethylidene-2-norbornene were placed in a dry, oxygen-free 300 ml V4A steel autoclave. At an internal temperature of 40° C., the pressure was increased from 4.0 bar to 6.0 bar by means of ethene. The catalyst employed comprised $2 \times 10^{-7}$ mol of $[(flu)Et_2PBPh_2(cp)ZrCl_2]$ and 0.66 ml of a 10% strength solution of MAO in toluene (2.0 mmol of Al). The catalyst was added via a pressure lock and the pressure was increased from 6.0 bar to 8.0 bar. The polymerization proceeded in the temperature range from 40° C. to 44° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 4.6 g |
| Catalyst activity: | 46.0 tonnes of EP rubber per mole of Zr and hour |
| FTIR: | |
| Propene: | 41% by weight |
| Ethene: | 54% by weight |
| ENB: | 5% by weight |
| Limiting viscosity in ortho-dichlorobenzene at 140° C.: | $[\eta] = 5.54$ dl/g |
| corresponding to a calculated mean molar mass $M_\eta$: | 680 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -49°$ C. |
| melting point: | $T_m = -3°$ C. |
| enthalpy of fusion: | $H_m = 18$ J/g |

EXAMPLE 24

Terpolymerization of Ethene, Propene and Ethylidenenorbornene 100 ml of dry toluene which had been distilled under inert gas, 10 g of propene and 2 g of 5-ethylidene-2-norbornene were placed in a dry, oxygen-free 300 ml V4A steel autoclave. At an internal temperature of 40° C., the pressure was increased from 3.0 bar to 5.0 bar by means of ethene. The catalyst employed comprised $1.5 \times 10^{-7}$ mol of $[(flu)Et_2PBPh_2(cp)ZrCl_2]$ and 0.99 ml of a 10% strength solution of MAO in toluene (1.5 mmol of Al). The catalyst was added via a pressure lock and the pressure was increased from 5.0 bar to 7.0 bar. The polymerization proceeded in the temperature range from 40° C. to 46° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 3.7 g |
| Catalyst activity: | 49.3 tonnes of EP rubber per mole of Zr and hour |
| FTIR: | |
| Propene: | 51% by weight |
| Ethene: | 45% by weight |
| ENB: | 4% by weight |
| Limiting viscosity in ortho-dichlorobenzene at 140° C.: | $[\eta] = 7.01$ dl/g |
| corresponding to a calculated mean molar mass $M_\eta$: | 949 kg/mol |
| derived from $[\eta] = k \cdot M^\alpha$ where $k = 4.00 \cdot 10^{-4}$ $\alpha = 0.710$ | |
| DSC: (2nd heating) | |
| glass transition temperature: | $T_g = -50°$ C. |
| melting point: | $T_m = -19°$ C. |
| enthalpy of fusion: | $H_m = 3$ J/g |
| GPC: (Universal calibration using polystyrene standards) | |
| | $M_w = 1.251$ kg/mol |
| | $M_n = 470$ kg/mol |
| | PD = 2.66 (monomodal) |

EXAMPLE 25

Terpolymerization of Ethene, Propene and Ethylidenenorbornene 100 ml of dry n-hexane which had been distilled under inert gas, 10 g of propene and 1 g of 5-ethylidene-2-norbornene were placed in a dry, oxygen-free 300 ml V4A steel autoclave. At an internal temperature of 60° C., the pressure was increased from 4 bar to 6 bar by means of ethene. The catalyst employed comprised $1.5 \times 10^{-7}$ mol of $[(flu)Et_2PBPh_2(cp)ZrCl_2]$ and 0.99 ml of a 10% strength solution of MAO in toluene (1.5 mmol of Al). The catalyst was added via a pressure lock and the pressure was increased from 6 bar to 8 bar. The polymerization proceeded in the temperature range from 60° C. to 64° C. and was stopped after 30 minutes. The polymer formed was stirred with ethanol/hydrochloric acid 90/10, filtered, washed with ethanol and dried to constant weight at 80° C. in a vacuum drying oven.

| | |
|---|---|
| Polymer yield: | 2.31 g |
| Catalyst activity: | 30.8 tonnes of EP rubber per mole of Zr and hour |
| FTIR: | |
| Propene: | 37% by weight |
| Ethene: | 55% by weight |
| ENB: | 8% by weight |
| Limiting viscosity in ortho-dichlorobenzene at 140° C.: | $[\eta] = 2.91$ dl/g |
| GPC: (universal calibration using polystyrene standards) | |
| bimodal distribution | $M_w$ 268 kg/mol |
| | $M_n = 60$ kg/mol |
| | $M_{peak1} = 233$ kg/mol |
| | $M_{peak2} = 17$ kg/mol |
| DSC: (2nd heating) | |
| glass transition temperature: | $T_g = -50°$ C. |
| melting point: | $T_m = -5°$ C. |
| enthalpy of fusion: | $H_m = 22$ J/g |

EXAMPLE 26

Ethene-Propene Copolymerization 100 ml of dry toluene which has been distilled under inert gas and 100 mg of undried montmorillonite K 10 (Fluka) which has been degassed in a high vacuum (10 minutes/$10^{-3}$ bar) and stored under argon, and 0.3 ml of 1 molar TIBA solution in toluene (=0.3 mmol of triisobutylaluminum)

were introduced into a dry, oxygen-free 300 ml V4A steel autoclave, and 10 g of propene were condensed in. At an internal temperature of 50° C., the pressure of 3.5 bar was increased to 6 bar with ethene. The catalyst used was a mixture of $1.7 \times 10^{-7}$ mol of [(flu)Et$_2$PBPh$_2$(cp)ZrCl$_2$], $3.3 \times 10^{-7}$ mol of [(cp)Et$_2$PBCl$_2$(cp)ZrCl$_2$] and 0.099 ml of 10% MAO solution in toluene (0.15 mmol of Al, Al/Zr=300). The catalyst was added via a pressure lock, and the pressure was increased from 6 bar to 8.5 bar with ethene. The polymerization at 50° C. was terminated after 30 minutes. The polymer formed was washed by stirring with ethanol/hydrochloric acid 90/10, filtered, washed with ethanol and dried in a vacuum drying cabinet at 80° C. to constant weight.

| | |
|---|---|
| Polymer yield: | 2.9 g |
| Catalyst activity: | 11.6 metric tons of EP rubber per mol of Zr and hour |
| Intrinsic viscosity in ortho-dichlorobenzene at 140° C.: | [η] = 2.27 dl/g |
| GPC analysis showed a copolymer with a bimodal distribution. | |
| GPC: (universal calibration using polystyrene standards) | |
| Component 1 (31% by weight): | M$_w$1 = 1,580 kg/mol<br>M$_n$1 = 857 kg/mol |
| Component 2: (69% by weight): | M$_w$2 = 107 kg/mol<br>M$_n$2 = 57 kg/mol |

EXAMPLE 27

Ethene-Propene Copolymerization 100 ml of dry toluene which has been distilled under inert gas and 100 mg of undried montmorillonite K 10 (Fluka) which has been degassed in a high vacuum (10 minutes/$10^{-3}$ bar) and stored under argon, and 0.3 ml of 1 molar TIBA solution in toluene (=0.3 mmol of triisobutylaluminum) were introduced into a dry, oxygen-free 300 ml V4A steel autoclave, and 10 g of propene were condensed in. At an internal temperature of 50° C., the pressure of 3.5 bar was increased to 6 bar with ethene. The catalyst used was a mixture of $3.5 \times 10^{-7}$ mol of [(flu)Et$_2$PBPh$_2$(cp)ZrCl$_2$], $1.5 \times 10^{-7}$ mol of [(cp)Et$_2$PBCl$_2$(cp)ZrCl$_2$] and 0.099 ml of 10% MAO solution in toluene (0.15 mmol of Al, Al/Zr=300). The catalyst was added via a pressure lock, and the pressure was increased from 6 bar to 8.5 bar with ethene. The polymerization at 50° C. was terminated after 30 minutes. The polymer formed was washed by stirring with ethanol/hydrochloric acid 90/10, filtered, washed with ethanol and dried in a vacuum drying cabinet at 80° C. to constant weight.

| | |
|---|---|
| Polymer yield: | 3.55 g |
| Catalyst activity: | 14.2 metric tons of EP rubber per mol of Zr and hour |
| Intrinsic viscosity in ortho-dichlorobenzene at 140° C.: | [η] = 4.88 dl/g |
| GPC analysis showed a copolymer with a bimodal distribution (FIG. 1). | |
| GPC: (universal calibration using polystyrene standards) | |
| Component 1 (64% by weight): | M$_w$1 = 1,617 kg/mol<br>M$_n$1 = 890 kg/mol |
| Component 2: (36% by weight): | M$_w$2 = 152 kg/mol<br>M$_n$2 = 68 kg/mol |

EXAMPLE 28

Ethene-Propene-Ethylidenenorbornene Terpolymerization

The polymerization was carried out as in Example 24, but in this experiment at 80° C.

| | |
|---|---|
| Polymer yield: | 1.1 g |
| Catalyst activity: | 14.7 metric tons of EP rubber per mol of Zr and hour |
| FTIR: | |
| Propene: | 41% by weight |
| Ethene: | 52% by weight |
| ENB: | 7% by weight |
| Intrinsic viscosity in ortho-dichlorobenzene at 140° C.: | [η] = 1.88 dl/g |
| corresponding to a calculated mean molecular weight M$_n$: | 149 kg/mol |
| from [η] = k · M$^\alpha$, where k = 4.00 · 10$^{-4}$ α = 0.710 | |
| DSC: (2nd heating) | |
| glass transition temperature: | T$_g$ = −49° C. |
| melting point: | T$_m$ = −16/59° C. |
| enthalpy of melting: | H$_m$ = 10 J/g |
| GPC analysis showed a copolymer with a bimodal distribution. | |
| GPC: (universal calibration using polystyrene standards) | M$_w$ = 188 kg/mol<br>M$_n$ = 26 kg/mol<br>PD = 7.32 |

EXAMPLE 29 a

Carbazolyldiphenylboranylcyclopentadienylzirconium Dichloride [(Carbazolyl)BPh$_2$(cp)ZrCl$_2$], [(Cl$_2$H$_8$N)B(C$_6$H$_5$)$_2$(C$_5$H$_4$)ZrCl$_2$]

A solution of 3.02 g (7.08 mmol) of Ph$_2$B(cp)ZrCl$_3$ in 150 ml of toluene was slowly added dropwise under an argon atmosphere to a suspension of 1.24 g (7.08 mmol) of carbazolyllithium in 50 ml of toluene at −78° C. The suspension changed color from dark brown to red. After 2 hours at room temperature, a virtually clear solution had formed and was filtered under argon. The filtrate was evaporated to half and stored at −20° C. for 16 hours. The resultant precipitate was separated off, 10 ml of hexane were added to the filtrate, and the precipitate was again separated off. The filtrate was evaporated to dryness, and the red-violet residue was dried to constant weight. Yield: 1.85 g (46.8% of theory)

The resultant crude catalyst was employed for the polymerization without further purification.

EXAMPLE 29 b

Ethene-Propene Copolymerization 100 ml of toluene which had been dried over 4 Å molecular sieve and saturated with argon, and 10 g of propene were introduced into a dry, oxygen-free 300 ml V4A steel autoclave. At an internal temperature of 40° C., the pressure was increased from 3 bar to 5 bar with ethene. The catalyst used was the crude catalyst obtained in Example 29a. 0.28 mg (=$5 \times 10^{-7}$ mol) of [(carbazolyl)BPh$_2$(cp)ZrCl$_2$] and 3.3 ml of 10% MAO solution in toluene (5 mmol of Al) were employed. The catalyst was added via a pressure lock, and the pressure was increased from 5 bar to 7 bar with ethene. The polymerization took place in the temperature range 40°–43° C. and was terminated after 30 minutes.

The polymer formed was washed by stirring with ethanol/hydrochloric acid 90/10, filtered, washed with ethanol and dried in a vacuum drying cabinet at 80° C. to constant weight.

| | |
|---|---|
| Polymer yield: | 2.3 g |
| Catalyst activity: | 9.2 metric tons of EP rubber per mol of Zr and hour |
| FTIR: | |
| Propene: | 29% by weight |
| Ethene: | 71% by weight |
| Intrinsic viscosity in ortho-dichlorobenzene at 140° C.: | $[\eta]$ = 2.12 dl/g |
| corresponding to a calculated mean molecular weight $M_n$: | 175 kg/mol |
| from $[\eta] = k \cdot M^\alpha$, where $k = 4.00 \cdot 10^{-4}$ $\alpha = 0.710$ | |
| DSC: (2nd heating) | |
| glass transition temperature: | $T_g$ = -46° C. |
| melting point: | $T_m$ = 71° C. |

COMPARATIVE EXAMPLE 1 (Polymerization of Propene)

About 1 mol of propene was placed in a dry, oxygen-free 300 ml V4A steel autoclave and the bulk polymerization was started at 20° C. by addition of the catalyst via a pressure lock. The catalyst employed comprised $1 \times 10^{-6}$ mol of [(Me$_3$Si-cp)Ph$_2$PBCl$_2$(Cp)ZrCl$_2$] and $1 \times 10^{-2}$ mol of MAO in 9 ml of toluene.

The internal temperature rose from 20° C. to 24° C. After one hour, work-up using ethanol/hydrochloric acid and drying gave 3.2 g of a rubber-like polypropylene.

| | |
|---|---|
| Catalyst activity: | 3.2 metric tonnes per mol·h |
| DSC: | amorphous PP, $T_g$ = -4° C. |
| GPC (polystyrene calibration): | $M_w$ = 143 kg/mol |
| | $M_n$ = 28 kg/mol |
| Limiting viscosity (o-Cl$_2$-benzene, 140° C.) | $\eta$ = 0.66 dl/g |
| NMR (triad analysis) | 37% isotactic |
| | 42% atactic |
| | 21% syndiotactic |

The significantly lower molar and catalyst activity are made clear in this example.

COMPARATIVE EXAMPLE 2 (Copolymerization of Ethene and Propene)

100 ml of dry toluene which had been distilled under inert gas and 10 g of propene were placed in a dry, oxygen-free 300 ml V4A steel autoclave. At 20° C., the catalyst was added under pressure via a pressure lock and the internal pressure was immediately increased from 2.5 bar to 6.5 bar by means of ethene. The internal temperature rose to 28° C. The catalyst employed was a mixture of $5 \times 10^{-7}$ mol of [(Me$_3$Si-cp)Ph$_2$PBCl$_2$(cp)ZrCl$_2$] and $5 \times 10^{-3}$ mol of methylaluminoxane (MAO) in 4.1 ml of toluene which had been preactivated at room temperature for about 10 minutes.

The polymerization was stopped after 30 minutes.

| | |
|---|---|
| Polymer yield: | 5.2 g |
| Catalyst activity: | 20.8 metric tonnes of EP rubber per mol of catalyst and hour |
| Limiting viscosity in ortho-dichlorobenzene at 140° C.: | $[\eta]$ = 1.51 dl/g |
| GPC in ortho-dichlorobenzene at 140° C.: | $M_w$ = 309 kg/mol, $M_n$ = 106 kg/mol |
| IR: | 46% by weight of propene, 54% by weight of ethene |
| DSC: | amorphous copolymer with $T_g$ = -55° C. |

In view of the low polymerization temperature, the molar mass is unsatisfactory since it will become significantly worse at higher polymerization temperatures.

COMPARATIVE EXAMPLE 3 (Terpolymerization of Ethene, Propene and Ethylidenenorbornene)

The procedure of Comparative Example 2 was repeated, but the catalyst employed comprised $5 \times 10^{-7}$ mol of rac-[(ind)Et$_2$PBCl$_2$(ind)ZrCl$_2$] activated with $5 \times 10^{-3}$ mol of (MAO). The internal pressure was increased by 2 bar by means of ethene. The polymerization took place in the presence of 1 g of ethylidenenorbornene (ENB). The terpolymer formed (1.5 g) contained 63% by weight of ethene, 35% by weight of propene, 2% by weight of ENB. The limiting viscosity in orthodichlorobenzene at 140° C. was 1.46 dl/g. The GPC measurement in o-Cl$_2$-benzene at 140° C. gave values of $M_w$=460 kg/mol, $M_n$=203 kg/mol. DSC analysis in the 2nd heating indicated an amorphous polymer having a glass transition temperature $T_g$=-50° C.

In view of the low polymerization temperature, the molar mass is unsatisfactory since it will become significantly worse at higher polymerization temperatures.

COMPARATIVE EXAMPLE 4 (Terpolymerization of Ethene, Propene and ENB)

The procedure of the preceding example was repeated, but the amount of MAO was only $1 \times 10^{-3}$ mol and the polymerization temperature was 40–45° C. The catalyst activity was 4.4 metric tonnes of EPDM per mol of catalyst and hour. The limiting viscosity (o-Cl$_2$-benzene, 140° C.) was 1.34 dl/g. The glass transition was at $T_g$=-52° C.

The low activity and molar mass is clear.

COMPARATIVE EXAMPLE 5 (Terpolymerization of Ethene, Propene and ENB)

The procedure of the preceding example was repeated, but the polymerization was carried out at 40–46° C. in the presence of 2 g of ENB and using $5 \times 10^{-3}$ mol of MAO. The catalyst activity was 11.2 metric tonnes of EPDM rubber per mol of catalyst and hour. The $\eta$ value (o-Cl$_2$-benzene, 140° C.) was 1.50 dl/g, $M_w$=302 kg/mol, $M_n$=112 kg/mol.

The copolymer composition was:
69% by weight of ethene, 28% by weight of propene, 3% by weight of ENB. The glass transition was at $T_g$=-42° C.

Low activity combined with unsatisfactory ENB incorporation.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the homopolymerization or copolymerization of one or more olefins, cycloolefins, isoolefins, alkynes or diolefins monomers comprising the step of admixing one or more monomer in the presence of at least one transition metal compounds having at least two ligands and at least one donor-acceptor interaction between the ligands, wherein at least one ligand is a fluorenyl ligand and the transition metal compound has at least one alkyl or aryl group on at least one acceptor atom and optionally one or more cocatalyst, wherein the process is carried out at a temperature from about −60 to about +250° C., wherein the process produces polymers having a mean viscosity molar mass $M_\eta$ greater than 500 kg/mol.

2. Process according to claim 1, wherein the transition metal compounds are applied to a support material.

3. Process according to claim 1, wherein the polymerization is carried out in the temperature range from 10° C. to 100° C.

4. Process according to claim 3, wherein the polymerisation is carried out in the temperature range 20° to 90° C.

5. Process according to claim 4 wherein the polymerisation is carried out in the temperature range from 30° C. to 80° C.

6. Process according to claim 1, wherein the ratio of cocatalyst to transition metal compound is in the range $\leq 100{,}000{:}1$.

7. Process according to claim 6, wherein the ratio of cocatalyst to transition metal compound is in the range $\leq 10{,}000{:}1$.

8. Process according to claim 7, wherein the ratio of cocatalyst to transition metal compound is in the range $\leq 1{,}000{:}1$.

9. Process according to claim 8, wherein the ratio of cocatalyst to transition metal compound is in the range $\leq 300{:}1$.

10. A process for preparing an elastomer comprising the step of admixing one or more monomer in the presence of at least one transition metal compound having at least two ligands and at least one donor-acceptor interaction between the ligands, wherein at least one ligand is a fluorenyl ligand and the transition metal compound has at least one alkyl or aryl group on at least one acceptor atom and optionally one or more cocatalyst, wherein the process is carded out at a temperature from about −60 to about +250° C., wherein the process produces polymers having a mean viscosity molar mass $M\eta$ greater than 500 kg/mol.

11. A process for preparing a polyolefin comprising the step of admixing one or more monomer in the presence of at least one transition metal compound having at least two ligands and at least one donor-acceptor interaction between the ligands, wherein at least one ligand is a fluorenyl ligand and the transition metal compound has at least one alkyl or aryl group on at least one acceptor atom and optionally one or more cocatalyst, wherein the process is carried out at a temperature from about −60 to about +250° C., wherein the process produces polymers having a mean viscosity molar mass $M_\eta$ greeter than 500 kg/mol.

12. The process according to claim 10, wherein the elastomer is an elastomeric polypropylene.

13. The process according to claim 10, wherein the elastomer prepared is selected from the group consisting of ethylene-propylene-diene copolymers, ethylene-butene-diene copolymers, ethylene-hexene-diene copolymers, ethylene-octene-diene copolymers or mixtures thereof.

14. The process according to claim 10, wherein the elastomer has long-chain branching.

15. The process according to claim 10, wherein the elastomer prepared has bimodal or multimodal molecular weight distribution.

16. The process according to claim 11, wherein the polyolefin has long-chain branching.

17. The process according to claim 11, wherein the polyolefin has bimodal or multimodal molecular weight distribution.

* * * * *